United States Patent
Bhirud et al.

(10) Patent No.: US 10,556,877 B2
(45) Date of Patent: Feb. 11, 2020

(54) PROCESS FOR PREPARATION OF DAPAGLIFLOZIN

(71) Applicant: Glenmark Life Sciences Limited, Solapur (IN)

(72) Inventors: Shekhar Bhaskar Bhirud, Mumbai (IN); Kumar Hari Bhushan, Gurgaon (IN); Raghu Ram Suraparaju, Hyderabad (IN); Nandkumar Gaikwad, Navi Mumbai (IN); Sharad Gore, Thane (IN); Rajendra Jagdhane, Pune (IN); Mandar Kulkarni, Pune (IN)

(73) Assignee: Glenmark Life Sciences Limited, Solapur (IN)

(*) Notice: Subject to any disclaimer, the term of this patent is extended or adjusted under 35 U.S.C. 154(b) by 0 days.

(21) Appl. No.: 15/571,112

(22) PCT Filed: May 4, 2016

(86) PCT No.: PCT/IB2016/052527
§ 371 (c)(1),
(2) Date: Nov. 1, 2017

(87) PCT Pub. No.: WO2016/178148
PCT Pub. Date: Nov. 10, 2016

(65) Prior Publication Data
US 2018/0127391 A1    May 10, 2018

(30) Foreign Application Priority Data

May 5, 2015   (IN) .................. 1790/MUM/2015
Jan. 20, 2016  (IN) .................. 201621002175

(51) Int. Cl.
| | |
|---|---|
| *C07D 309/10* | (2006.01) |
| *A61K 31/70* | (2006.01) |
| *B01D 9/00* | (2006.01) |
| *C07B 51/00* | (2006.01) |
| *C07B 63/04* | (2006.01) |
| *C07C 31/20* | (2006.01) |
| *C07H 7/04* | (2006.01) |

(52) U.S. Cl.
CPC ............ *C07D 309/10* (2013.01); *A61K 31/70* (2013.01); *B01D 9/0054* (2013.01); *C07B 51/00* (2013.01); *C07B 63/04* (2013.01); *C07C 31/207* (2013.01); *C07H 7/04* (2013.01)

(58) Field of Classification Search
CPC .................................................... C07D 309/10
USPC ........................................................ 549/423
See application file for complete search history.

(56) References Cited

U.S. PATENT DOCUMENTS

| | | | | |
|---|---|---|---|---|
| 8,999,941 | B2* | 4/2015 | Henschke | ............ C07D 409/00 514/23 |
| 9,394,328 | B2* | 7/2016 | Blatter | ...................... C07H 7/04 |
| 9,845,303 | B2* | 12/2017 | Desai | ................... C07D 309/10 |
| 2002/0137903 | A1 | 9/2002 | Ellsworth et al. | |
| 2007/0238866 | A1 | 10/2007 | Deshpande et al. | |
| 2013/0046088 | A1 | 2/2013 | Liou et al. | |
| 2013/0237487 | A1* | 9/2013 | Henschke | ............ C07D 409/00 514/23 |
| 2013/0303467 | A1 | 11/2013 | Gougoutas et al. | |
| 2016/0256433 | A1* | 9/2016 | Staric | ................... A61K 9/1635 |

FOREIGN PATENT DOCUMENTS

| | | | | |
|---|---|---|---|---|
| CN | 104478839 | A | | 4/2015 |
| WO | WO 2004063209 | | * | 7/2004 |
| WO | WO 2010022313 | | * | 2/2010 ........... C07D 309/10 |

* cited by examiner

*Primary Examiner* — Nizal S Chandrakumar
(74) *Attorney, Agent, or Firm* — Ryan, Mason & Lewis, LLP

(57) ABSTRACT

The present invention relates to a process for the preparation of amorphous dapagliflozin. The present invention relates to 2,3-butanediol solvate of dapagliflozin and process for its preparation.

2 Claims, 4 Drawing Sheets

PROCESS FOR PREPARATION OF DAPAGLIFLOZIN

PRIORITY

This application claims priority under 35 U.S.C. § 371 to International Application No. PCT/IB2016/052527, filed May 4, 2016 which claims the benefit of Indian Provisional Application 1790/MUM/2015 filed May 5, 2015, and entitled "PROCESS FOR PREPARATION OF DAPAGLIFLOZIN" and Indian Provisional Application 201621002175 filed Jan. 20, 2016, and entitled "PROCESS FOR PREPARATION OF DAPAGLIFLOZIN", the contents of which are incorporated herein by reference.

BACKGROUND OF THE INVENTION

Technical Field

The present invention relates to a process for the preparation of amorphous dapagliflozin. The present invention relates to 2,3-butanediol solvate of dapagliflozin and process for its preparation.

Description of the Related Art

Dapagliflozin, also known as D-glucitol, 1,5-anhydro-1-C-[4-chloro-3-[(4-ethoxyphenyl)methyl]phenyl]-, (1S)-, is represented by the structure of formula I.

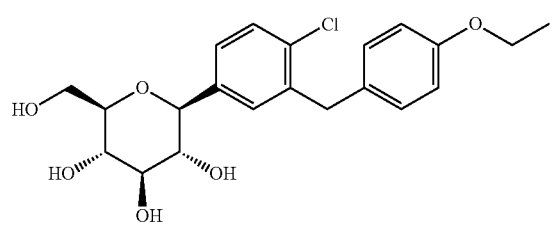

The process for the preparation of dapagliflozin involves the step of silylation of D-glucono-1,5-lactone, a compound of formula IV to give 2,3,4,6-tetra-O-(trimethylsilyl)-D-glucono-1,5-lactone, a compound of formula V.

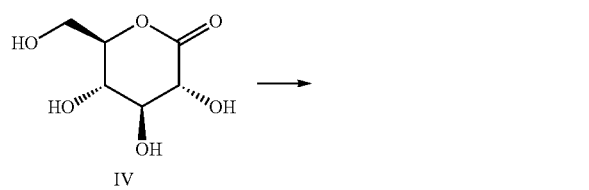

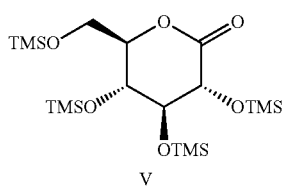

The processes known in the art involve use of trimethylsilyl chloride (TMSCl) for silylation of the compound of formula IV. The present invention provides a process wherein hexamethyldisilazane (HMDS) is used instead of TMSCl for silylation of the compound of formula IV. With use of HMDS, the by-product is ammonia which does not degrade the product. Further, with use of hexamethyldisilazane, the reaction becomes one-pot and the work-up is easier as water is not used during work-up of the reaction.

The object of the present invention is to provide a process for the preparation of amorphous dapagliflozin with high purity.

SUMMARY OF THE INVENTION

The present invention provides a process for the preparation of dapagliflozin in amorphous form, the process comprising:

(a) reducing a compound of formula II to a compound of formula III in the presence of a Lewis acid;

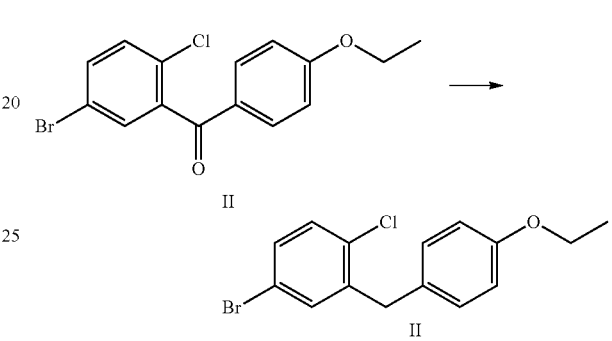

(b) silylating a compound of formula IV with hexamethyldisilazane to form a compound of formula V;

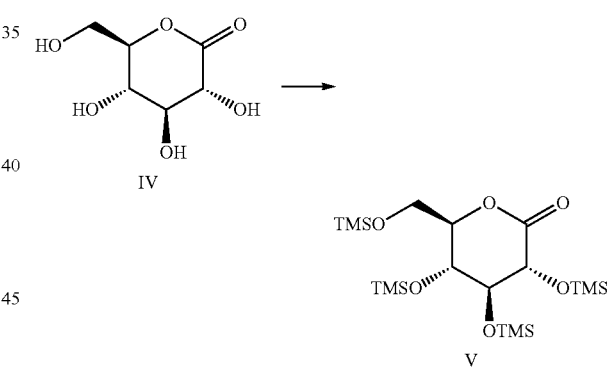

(c) reacting the compound of formula III with the compound of formula V in the presence of a strong base followed by treatment with an acid in the presence of an alcohol to prepare a compound of formula VII, wherein R is an alkyl group selected from $C_{1-5}$ alkyl;

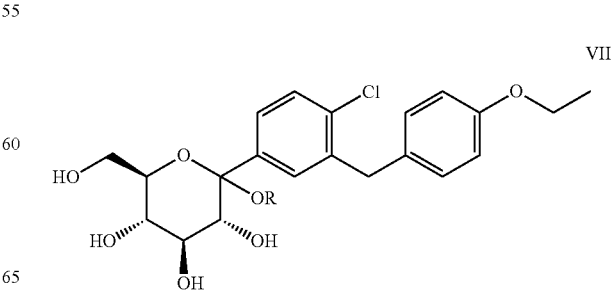

(d) converting the compound of formula VII to dapagliflozin;
(e) acetylating dapagliflozin to give D-glucitol, 1,5-anhydro-1-C-[4-chloro-3-[(4-ethoxyphenyl)methyl]phenyl]-, 2,3,4,6-tetraacetate, (1S)-, a compound of formula VIII;

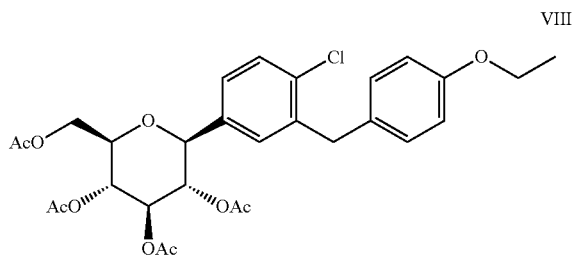 [SMILES: CCOc1ccc(Cc2cc([C@@H]3O[C@H](COC(C)=O)[C@@H](OC(C)=O)[C@H](OC(C)=O)[C@H]3OC(C)=O)ccc2Cl)cc1]

(f) optionally, purifying the compound of formula VIII with a solvent selected from halogenated hydrocarbons, alcohols, ethers, or mixtures thereof;
(g) hydrolyzing the compound of formula VIII obtained in step (f) to give dapagliflozin;
(h) dissolving dapagliflozin of step (g) in a solvent selected from halogenated hydrocarbons, alcohols, hydrocarbons, or mixtures thereof to form a solution; and
(i) recovering amorphous dapagliflozin from the solution of step (h).

In another embodiment, the present invention provides a process for the preparation of dapagliflozin in amorphous form, the process comprising:
(i) dissolving dapagliflozin in isopropyl alcohol to form a solution;
(ii) optionally, completely evaporating isopropyl alcohol from the solution of step (i) to give a residue;
(iii) adding cyclohexane to the solution of step (i) or the residue of step (ii); and
(iv) isolating amorphous dapagliflozin.

In another embodiment, the present invention provides a process for the preparation of D-glucitol, 1,5-anhydro-1-C-[4-chloro-3-[(4-ethoxyphenyl)methyl]phenyl]-, 2,3,4,6-tetraacetate, (1S)-, a compound of formula VIII, in a purity of ≥99.6% and wherein the level of impurity G and impurity H is less than 0.15%,

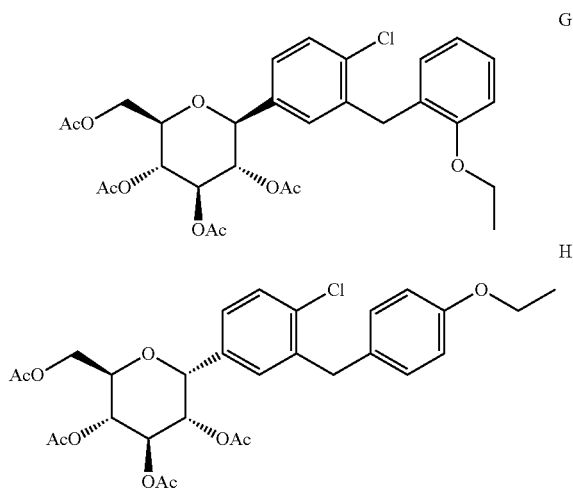

the process comprising:
(a) treating the compound of formula VIII with an ether solvent to form a reaction mass;
(b) heating the reaction mass of step (a);
(c) cooling the reaction mass of step (b);
(d) obtaining the compound of formula VIII from the reaction mass of step (c);
(e) optionally, crystallizing the compound of formula VIII obtained in step (d) with an alcohol solvent; and
(f) isolating the compound of formula VIII with a purity of ≥99.6% and wherein the level of impurity G and impurity H is less than 0.15%.

In another embodiment, the present invention provides a crystalline 2,3-butanediol solvate of dapagliflozin characterized by an X-ray powder diffraction (XRPD) spectrum having peak reflections at about 3.7, 9.6, 14.7, 16.7 and 18.4±0.2 degrees 2 theta.

In another embodiment, the present invention provides a process for the preparation of crystalline 2,3-butanediol solvate of dapagliflozin, the process comprising:
(a) treating dapagliflozin with 2,3-butanediol, optionally in the presence of a solvent, to form a solution;
(b) obtaining crystalline 2,3-butanediol solvate of dapagliflozin from the solution of step (a); and
(c) isolating the crystalline 2,3-butanediol solvate of dapagliflozin.

In another embodiment, the present invention provides a process for the preparation of dapagliflozin in amorphous form, the process comprising:
(a) dissolving 2,3-butanediol solvate of dapagliflozin in a solvent to form a solution; and
(b) recovering dapagliflozin in amorphous form from the solution of step (a).

In another embodiment, the present invention provides use of 2,3-butanediol solvate of dapagliflozin in the preparation of amorphous dapagliflozin.

DETAILED DESCRIPTION OF THE INVENTION

Figure 1:
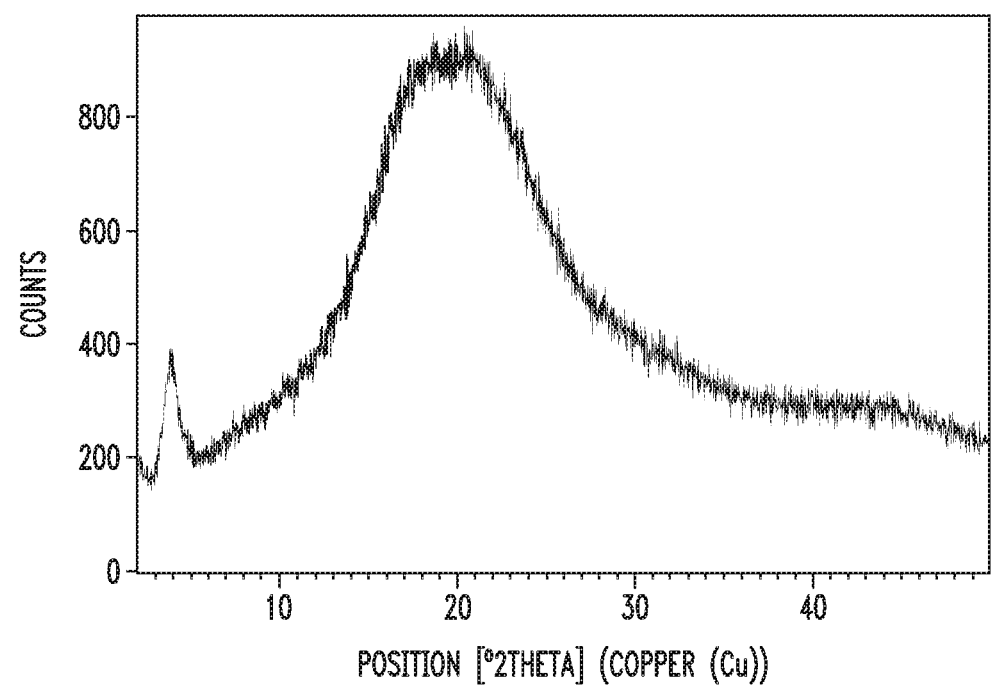
FIG. 1 is a characteristic XRPD of amorphous dapagliflozin as obtained in example 42.

The present invention provides a process for the preparation of dapagliflozin in amorphous form, the process comprising:
(a) reducing a compound of formula II to a compound of formula III in the presence of a Lewis acid;

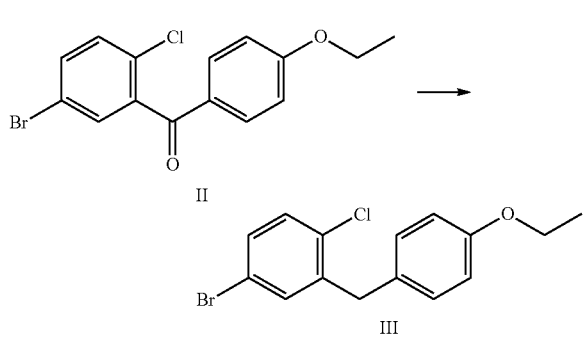

(b) silylating a compound of formula IV with hexamethyldisilazane to form a compound of formula V;

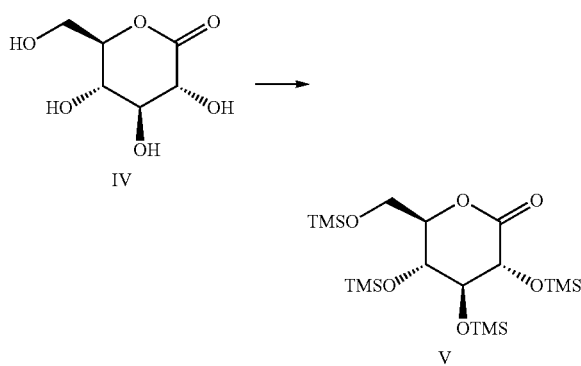

(c) reacting the compound of formula III with the compound of formula V in the presence of a strong base followed by treatment with an acid in the presence of an alcohol to prepare a compound of formula VII, wherein R is an alkyl group selected from $C_{1-5}$ alkyl;

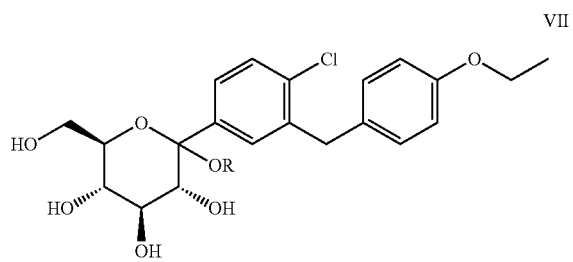

(d) converting the compound of formula VII to dapagliflozin;
(e) acetylating dapagliflozin to give D-glucitol, 1,5-anhydro-1-C-[4-chloro-3-[(4-ethoxyphenyl)methyl]phenyl]-, 2,3,4,6-tetraacetate, (1S)-, a compound of formula VIII;

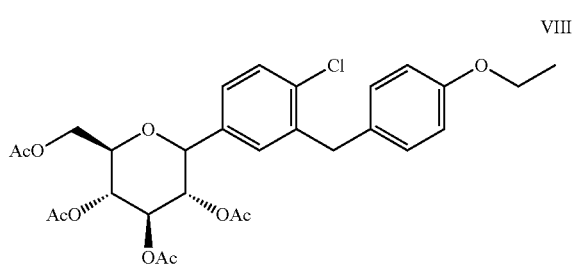 [SMILES: CCOc1ccc(Cc2cc(C3O[C@H](COC(C)=O)[C@@H](OC(C)=O)[C@H](OC(C)=O)[C@H]3OC(C)=O)ccc2Cl)cc1]

(f) optionally, purifying the compound of formula VIII with a solvent selected from halogenated hydrocarbons, alcohols, ethers, or mixtures thereof;
(g) hydrolyzing the compound of formula VIII obtained in step (f) to give dapagliflozin;
(h) dissolving dapagliflozin of step (g) in a solvent selected from halogenated hydrocarbons, alcohols, hydrocarbons, or mixtures thereof to form a solution; and
(i) recovering amorphous dapagliflozin from the solution of step (h).

In the present application, the term "room temperature" means a temperature of about 25° C. to about 30° C.

In (a) of the process for the preparation of dapagliflozin in amorphous form, the compound of formula II is reduced to the compound of formula III in the presence of a Lewis acid.

The Lewis acid may be selected from the group consisting of aluminium chloride, boron trifluoride, titanium tetrachloride and ferric chloride.

The reaction may be performed in the presence of a suitable solvent. The suitable solvent may include a nitrile such as acetonitrile, propionitrile and the like; an ester such as methyl acetate, ethyl acetate, n-propyl acetate, isopropyl acetate, tert-butyl acetate and the like; a halogenated hydrocarbon such as methylene dichloride, chloroform, ethylene dichloride and the like; an ether such as dimethyl ether, diethyl ether, diisopropyl ether, methyl tert-butyl ether, tetrahydrofuran, dioxane and the like; an aromatic hydrocarbon such as toluene and the like; an aliphatic hydrocarbon such as n-hexane, n-heptane and the like; dimethylformamide; dimethylsulfoxide; dimethylacetamide; N-methylpyrrolidone; water; or mixtures thereof.

The reduction of the compound of formula II may be performed with a reducing agent, for example triethylsilane.

In one embodiment, step (a) comprises reducing the compound of formula II with triethylsilane in presence of boron trifluoride in a mixture of methylene dichloride and acetonitrile to give the compound of formula III. After completion of reaction, the reaction mass is quenched with sodium bicarbonate solution. The layers may be separated and the aqueous layer may then be extracted with a solvent. The solvent used is as discussed supra, preferably an ester solvent like ethyl acetate. The extraction solvent may be removed. The mass obtained may be purified by a hydrocarbon solvent followed by an alcohol solvent. The hydrocarbon solvent may be an aromatic or an aliphatic hydrocarbon solvent as discussed supra, for example toluene and the alcohol solvent may include methanol, ethanol, n-propyl alcohol, isopropyl alcohol, n-butyl alcohol and the like, for example methanol.

In (b) of the process for the preparation of dapagliflozin in amorphous form, the compound of formula IV is silylated with hexamethyldisilazane to form the compound of formula V.

The reaction may be performed in the presence of a suitable solvent. The suitable solvent may include a nitrile such as acetonitrile, propionitrile and the like; an ester such as methyl acetate, ethyl acetate, n-propyl acetate, isopropyl acetate, tert-butyl acetate and the like; a halogenated hydrocarbon such as methylene dichloride, chloroform, ethylene dichloride and the like; an ether such as dimethyl ether, diethyl ether, diisopropyl ether, methyl tert-butyl ether, tetrahydrofuran, dioxane and the like; an aromatic hydrocarbon such as toluene and the like; an aliphatic hydrocarbon such as n-hexane, n-heptane and the like; dimethylformamide; dimethylsulfoxide; dimethylacetamide; N-methylpyrrolidone; water; or mixtures thereof.

In one embodiment, step (b) may be performed in presence of a suitable catalyst, for example iodine.

In one embodiment, step (b) comprises silylating the compound of formula IV with hexamethyldisilazane in presence of methylene dichloride as solvent and iodine as catalyst to form the compound of formula V. After completion of reaction, the reaction mass is filtered through hyflo bed and the filtrate is concentrated to remove the solvent. The compound of formula V is then distilled out under vacuum.

In (c) of the process for the preparation of dapagliflozin in amorphous form, the compound of formula III is reacted with the compound of formula V in the presence of a strong base.

The strong base may include an alkyl lithium such as methyl lithium, n-butyl lithium, lithium diisopropylamide and lithium bis(trimethylsilyl)amide.

The reaction may be performed in the presence of a suitable solvent. The suitable solvent may include a nitrile such as acetonitrile, propionitrile and the like; an ester such as methyl acetate, ethyl acetate, n-propyl acetate, isopropyl acetate, tert-butyl acetate and the like; a halogenated hydrocarbon such as methylene dichloride, chloroform, ethylene dichloride and the like; an ether such as dimethyl ether, diethyl ether, diisopropyl ether, methyl tert-butyl ether, tetrahydrofuran, dioxane and the like; an aromatic hydrocarbon such as toluene and the like; an aliphatic hydrocarbon such as n-hexane, n-heptane and the like; dimethylformamide; dimethylsulfoxide; dimethylacetamide; N-methylpyrrolidone; water; or mixtures thereof.

In one embodiment, step (c) comprises reacting the compound of formula III with the compound of formula V in the presence of a strong base to obtain a compound of formula VI; and reacting the compound of formula VI with an acid in the presence of an alcohol to prepare the compound of formula VII wherein R is an alkyl group selected from $C_{1-5}$ alkyl

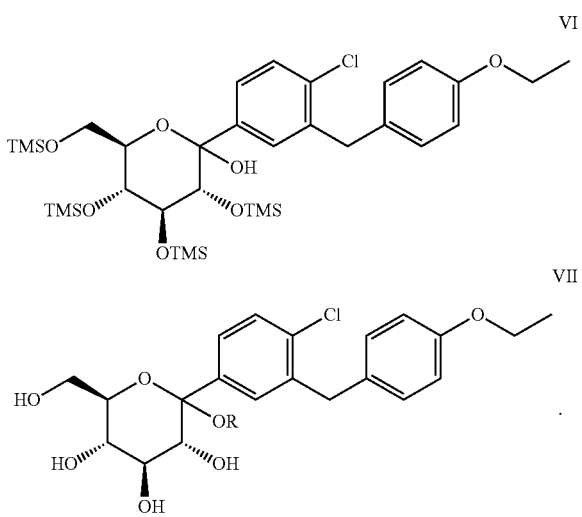

In one embodiment, the alcohol may be a $C_{1-5}$ alcohol. $C_{1-5}$ alcohol, for example, may include methanol, ethanol, n-propyl alcohol, isopropyl alcohol, n-butyl alcohol, isobutyl alcohol, n-pentyl alcohol and the like.

In one embodiment, the acid may be a sulfonic acid which may include methanesulfonic acid, benzenesulfonic acid and the like.

In one embodiment, the acid used in step (c) is methanesulfonic acid.

In one embodiment, step (c) comprises reacting the compound of formula III with the compound of formula V in presence of n-butyl lithium in tetrahydrofuran, followed by treatment with methanesulfonic acid in presence of methanol to prepare the compound of formula VII, wherein R is methyl.

In one embodiment, step (c) comprises reacting the compound of formula III with the compound of formula V in presence of n-butyl lithium in tetrahydrofuran to prepare the compound of formula VI which is further reacted with methane sulfonic acid in presence of methanol to prepare the compound of formula VII, wherein R is methyl.

After treatment with methanesulfonic acid in methanol, the reaction mass may be basified with a base. The base used may be an inorganic base. The inorganic base may include an alkali or an alkaline earth metal hydroxide, an alkali or an alkaline earth metal carbonate and the like, for example sodium hydroxide, potassium hydroxide, sodium carbonate, potassium carbonate and the like. The reaction mass may then be extracted with a solvent. The solvent used is as discussed supra, preferably an ester solvent like ethyl acetate. The extraction solvent may be removed. The mass so obtained may be purified using a suitable solvent. The suitable solvent used is as discussed supra. In one embodiment, the solvent used for purification is a mixture of an aromatic and an aliphatic hydrocarbon, preferably a mixture of toluene and cyclohexane.

In one embodiment, the compound of formula V may be isolated before further treatment.

In one embodiment, the compound of formula VI may be isolated before further treatment.

In one embodiment, the compound of formula VII may be isolated before further treatment.

In one embodiment, the compound of formula VI may not be isolated.

In one embodiment, steps (b) and (c) may be performed as one-pot process.

In (d) of the process for the preparation of dapagliflozin in amorphous form, the compound of formula VII is converted to dapagliflozin.

The reaction may be carried out in the presence of a reducing agent, for example triethylsilane.

The reaction may be carried out in the presence of a Lewis acid selected from the group consisting of aluminium chloride, boron trifluoride, titanium tetrachloride and ferric chloride.

The reaction may be performed in the presence of a suitable solvent. The suitable solvent may include a nitrile such as acetonitrile, propionitrile and the like; an ester such as methyl acetate, ethyl acetate, n-propyl acetate, isopropyl acetate, tert-butyl acetate and the like; a halogenated hydrocarbon such as methylene dichloride, chloroform, ethylene dichloride and the like; an ether such as dimethyl ether, diethyl ether, diisopropyl ether, methyl tert-butyl ether, tetrahydrofuran, dioxane and the like; an aromatic hydrocarbon such as toluene and the like; an aliphatic hydrocarbon such as n-hexane, n-heptane and the like; dimethylformamide; dimethylsulfoxide; dimethylacetamide; N-methylpyrrolidone; water; or mixtures thereof.

In one embodiment, step (d) comprises reducing the compound of formula VII with triethylsilane in presence of boron trifluoride in a mixture of methylene dichloride and acetonitrile to give dapagliflozin. After completion of reaction, the reaction mass is quenched with sodium bicarbonate solution. The layers may be separated and the aqueous layer may then be extracted with a solvent. The solvent used is as discussed supra, preferably an ester solvent like ethyl acetate. The extraction solvent may be removed.

In (e) of the process for the preparation of dapagliflozin in amorphous form, dapagliflozin is acetylated to give D-glucitol, 1,5-anhydro-1-C-[4-chloro-3-[(4-ethoxyphenyl)methyl]phenyl]-, 2,3,4,6-tetraacetate, (1S)-, the compound of formula VIII.

The acetylating agent includes, but is not limited to acetyl chloride, acetic anhydride.

The reaction may be carried out in the presence of a suitable base. The suitable base includes, but is not limited to alkali metal hydroxides such as lithium hydroxide, sodium hydroxide, potassium hydroxide; alkaline earth metal hydroxides; alkali metal carbonates such as sodium carbonate, potassium carbonate, alkaline earth metal carbonates; alkali metal bicarbonates such as sodium bicarbonate; tertiary amines such as triethylamine, NN-diisopropylethylamine; ammonia, pyridine, piperidine, 4-dimethylaminopyridine. Preferably the base selected is N,N-diisopropylethylamine, 4-dimethylaminopyridine.

The reaction may be carried out in the presence of a suitable solvent. The suitable solvent includes, but is not limited to halogenated hydrocarbons such as methylene dichloride, chloroform and the like; ethers such as dimethyl ether, diethyl ether, diisopropyl ether, tert-butyl methyl ether, tetrahydrofuran, dioxane and the like; hydrocarbons such as toluene, xylene and the like; dimethylsulfoxide; dimethylformamide; dimethylacetamide; N-Methyl-2-pyrrolidone; or mixtures thereof. Preferably the solvent selected is methylene dichloride.

In one embodiment, step (e) comprises acetylating dapagliflozin using acetic anhydride and N,N-diisopropylethylamine in presence of 4-dimethylaminopyridine in methylene dichloride. After completion of reaction, the reaction mass may be quenched with water. The organic layer may be separated, washed with sodium bicarbonate solution and concentrated.

In one embodiment, the compound of formula VIII is optionally purified with a solvent selected from halogenated hydrocarbons, alcohols, ethers, or mixtures thereof.

In (f) of the process for the preparation of dapagliflozin in amorphous form, the compound of formula VIII is purified with a solvent selected from halogenated hydrocarbons, alcohols, ethers, or mixtures thereof.

In one embodiment, halogenated hydrocarbons may include methylene dichloride, chloroform, ethylene dichloride and the like; alcohols may include methanol, ethanol, n-propyl alcohol, isopropyl alcohol, n-butyl alcohol and the like; and ethers may include dimethyl ether, diethyl ether, diisopropyl ether, methyl tert-butyl ether, tetrahydrofuran, dioxane and the like.

In one embodiment, the alcohol is methanol and the ether is diisopropyl ether.

In one embodiment, the present invention provides a process for the purification of the compound of formula VIII, the process comprising:
(i) treating the compound of formula VIII with methanol to form a reaction mass;
(ii) heating the reaction mass of step (i);
(iii) cooling the reaction mass of step (ii);
(iv) isolating the compound of formula VIII from the reaction mass of step (iii);
(v) treating the compound of formula VIII obtained in step (iv) with diisopropyl ether to form a reaction mass;
(vi) heating the reaction mass of step (v);
(vii) cooling the reaction mass of step (vi);
(viii) isolating the compound of formula VIII from the reaction mass of step (vii);
(ix) treating the compound of formula VIII obtained in step (viii) with methanol to form a reaction mass;
(x) heating the reaction mass of step (ix);
(xi) cooling the reaction mass of step (x);
(xii) isolating the compound of formula VIII from the reaction mass of step (xi).

The reaction mass of step (ii) may be optionally treated with charcoal and filtered.

In (g) of the process for the preparation of dapagliflozin in amorphous form, the compound of formula VIII obtained in step (f) is hydrolyzed to give dapagliflozin.

The reaction may be carried out in the presence of a suitable base. The suitable base includes, but is not limited to alkali metal hydroxides such as lithium hydroxide, sodium hydroxide, potassium hydroxide; alkaline earth metal hydroxides; alkali metal carbonates such as sodium carbonate, potassium carbonate, caesium carbonate; alkaline earth metal carbonates; alkali metal bicarbonates such as sodium bicarbonate. Preferably the base selected is sodium hydroxide.

The reaction may be carried out in the presence of a suitable solvent. The suitable solvent includes, but is not limited to alcohols such as methanol, ethanol, n-propyl alcohol, isopropyl alcohol, n-butyl alcohol and the like; ethers such as tetrahydrofuran, dioxane and the like; esters such as methyl acetate, ethyl acetate, n-propyl acetate, tert-butyl acetate and the like; halogenated hydrocarbons such as methylene dichloride, chloroform, ethylene dichloride and the like; water or mixtures thereof. Preferably the solvent selected is tetrahydrofuran-methanol-water mixture.

In one embodiment, step (g) comprises hydrolyzing the compound of formula VIII obtained in step (f) in presence of sodium hydroxide in tetrahydrofuran-methanol-water mixture. After completion of reaction, the reaction mass may be concentrated and treated with aqueous hydrochloric acid. The reaction mass may then be extracted with a solvent. The solvent used is as discussed supra, preferably a halogenated hydrocarbon solvent like methylene dichloride. The extraction solvent may be removed to give dapagliflozin.

In (h) of the process for the preparation of dapagliflozin in amorphous form, dapagliflozin of step (g) is dissolved in a solvent selected from halogenated hydrocarbons, alcohols, hydrocarbons, or mixtures thereof to form a solution.

In one embodiment, the halogenated hydrocarbon solvent may include methylene dichloride, chloroform, ethylene dichloride and the like; the alcohol solvent may include methanol, ethanol, n-propyl alcohol, isopropyl alcohol, n-butyl alcohol and the like; and the hydrocarbon solvent may be an aromatic or an aliphatic hydrocarbon solvent such as toluene, n-hexane, n-heptane, cyclohexane and the like.

In one embodiment, the alcohol is isopropyl alcohol and the hydrocarbon is cyclohexane.

Suitable temperature for dissolution of dapagliflozin in the solvent may range from about 25° C. to about the reflux temperature of the solvent. Stirring may be continued for any desired time period to achieve a complete dissolution of the compound. The stirring time may range from about 30 minutes to about 1 hour, or longer. The solution may be optionally treated with charcoal and filtered to get a particle-free solution.

In (i) of the process for the preparation of dapagliflozin in amorphous form, amorphous dapagliflozin is recovered from the solution of step (h).

In one embodiment, dapagliflozin in amorphous form is recovered by removing the solvent from the solution obtained in step (h). Removal of solvent may be accomplished by substantially complete evaporation of the solvent or concentrating the solution, cooling the solution if required and filtering the obtained solid. The solution may also be completely evaporated in, for example, a rotavapor, a vacuum paddle dryer or in a conventional reactor under vacuum above about 720 mm Hg, or evaporated by lyophilisation, freeze-drying technique, spray drying, fluid bed drying, flash drying, spin flash drying, thin-film drying.

In one embodiment, dapagliflozin in amorphous form is recovered by adding an anti-solvent to the solution obtained in step (h) to form a mixture and optionally, cooling and stirring the obtained mixture. The stirring time may range from about 30 minutes to about 10 hours, or longer. The temperature may range from about 0° C. to about 30° C.

The anti-solvent is selected such that dapagliflozin in amorphous form is precipitated out from the solution.

In one embodiment, dapagliflozin is dissolved in isopropyl alcohol to form a solution. Cyclohexane was then added to the solution and the obtained mixture was stirred and filtered to give amorphous dapagliflozin.

In one embodiment, dapagliflozin is dissolved in isopropyl alcohol to form a solution. The solution was then concentrated by completely evaporating isopropyl alcohol from the solution to obtain a residue. To the residue, cyclohexane was added and the obtained mixture was stirred and filtered to give amorphous dapagliflozin.

In one embodiment, the amorphous dapagliflozin is jet milled.

In one embodiment, the amorphous dapagliflozin is obtained in a purity of ≥99.8% and wherein the level of impurity A and impurity B is less than 0.15%

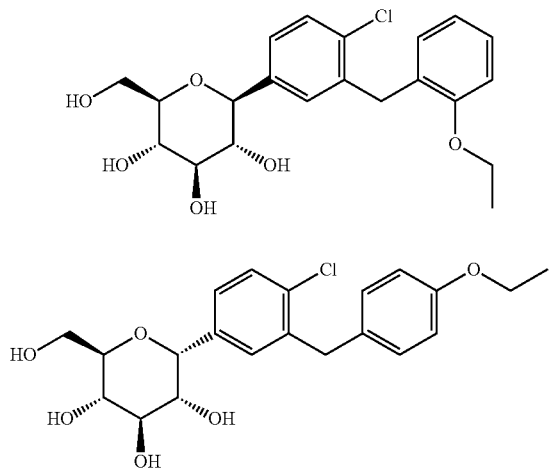

In one embodiment, the present invention provides a process for the preparation of dapagliflozin in amorphous form, the process comprising:
(i) dissolving dapagliflozin in isopropyl alcohol to form a solution;
(ii) optionally, completely evaporating isopropyl alcohol from the solution of step (i) to give a residue;
(iii) adding cyclohexane to the solution of step (i) or the residue of step (ii); and
(iv) isolating amorphous dapagliflozin.

The amorphous dapagliflozin is isolated by any method known in the art. The method, may involve any of techniques, known in the art, including filtration by gravity or by suction, centrifugation, and the like.

In one embodiment, the present invention provides a process for the preparation of D-glucitol, 1,5-anhydro-1-C [4-chloro-3-[(4-ethoxyphenyl)methyl]phenyl]-, 2,3,4,6-tetraacetate, (1S)-, a compound of formula VIII, in a purity of ≥99.6% and wherein the level of impurity G and impurity H is less than 0.15%,

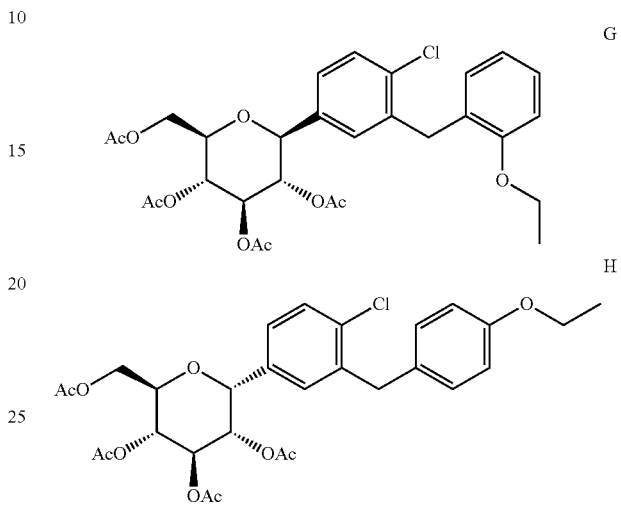

the process comprising:
(a) treating the compound of formula VIII with an ether solvent to form a reaction mass;
(b) heating the reaction mass of step (a);
(c) cooling the reaction mass of step (b);
(d) obtaining the compound of formula VIII from the reaction mass of step (c);
(e) optionally, crystallizing the compound of formula VIII obtained in step (d) with an alcohol solvent; and
(f) isolating the compound of formula VIII with a purity of ≥99.6% and wherein the level of impurity G and impurity H is less than 0.15%.

In one embodiment, the ether solvent may include diethyl ether, diisopropyl ether, methyl tert-butyl ether, tetrahydrofuran, dioxane and the like; the alcohol solvent may include methanol, ethanol, n-propyl alcohol, isopropyl alcohol, n-butyl alcohol and the like.

In one embodiment, the alcohol is methanol and the ether is diisopropyl ether.

In one embodiment, the process further comprises converting the compound of formula VIII to amorphous dapagliflozin as discussed supra.

In one embodiment, the present invention provides use of the compound of formula VIII, as obtained by above process, in the preparation of dapagliflozin.

The present invention provides the compound of formula VIII wherein the level of impurity G and impurity H is less than 0.15% w/w relative to the amount of the compound of formula VIII, obtained by above process, as analyzed by chemical purity using high performance liquid chromatography (HPLC) with the conditions described below:

Reagents and Solvents: Sodium perchlorate monohydrate (AR grade), Perchloric acid 70% (AR grade), Acetonitrile (HPLC grade), Water (Milli Q or equivalent) Chromatographic Conditions:

Apparatus: A High Performance Liquid Chromatograph equipped with quaternary gradient pumps, variable wavelength UV detector attached with data recorder and integrator software.

Column: Inertsil ODS 3V, 250×4.6 mm, 5μ; Column temperature: 25° C.
Sample Cooler temperature: 25° C.
Mobile Phase A: Buffer; Buffer: 0.01M Sodium perchlorate monohydrate in water. Adjust pH 2.5 with diluted Perchloric acid.
Mobile Phase B: Acetonitrile

| Time (min.) | % Mobile Phase A | % Mobile Phase B |
|---|---|---|
| 0.01 | 70 | 30 |
| 30 | 60 | 40 |
| 35 | 50 | 50 |
| 70 | 15 | 85 |
| 85 | 15 | 85 |
| 95 | 70 | 30 |

Diluent: Acetonitrile: Water (1:1, v/v)
Flow Rate: 1.0 mL/min
Detection: UV 220 nm
Injection Volume: 10 μL
The retention time of the compound of formula VIII is about 61.0 minutes under these conditions.
Relative retention time for impurity G is about 1.03 and impurity H is about 1.05 with respect to the compound of formula VIII.

In one embodiment, the present invention provides a process for the purification of dapagliflozin wherein, the process comprises purification of crude dapagliflozin from a halogenated hydrocarbon. The halogenated hydrocarbon used may include methylene dichloride, chloroform, ethylene dichloride and the like.

In one embodiment, crude dapagliflozin is purified from methylene dichloride.

In one embodiment, the present invention provides dapagliflozin substantially free of the following compounds:

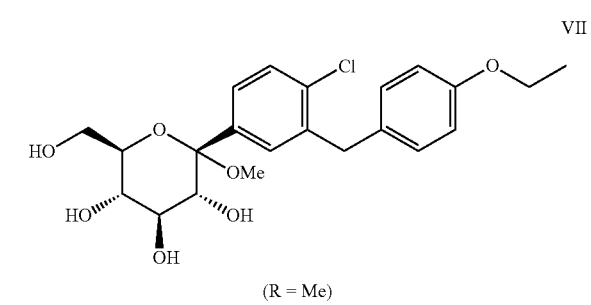

(R = Me)

VII

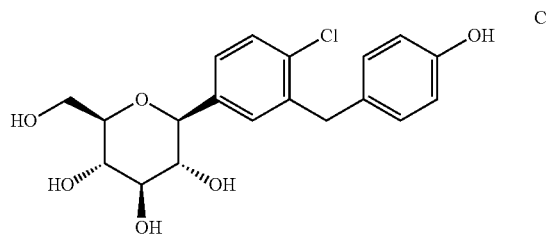

C

D

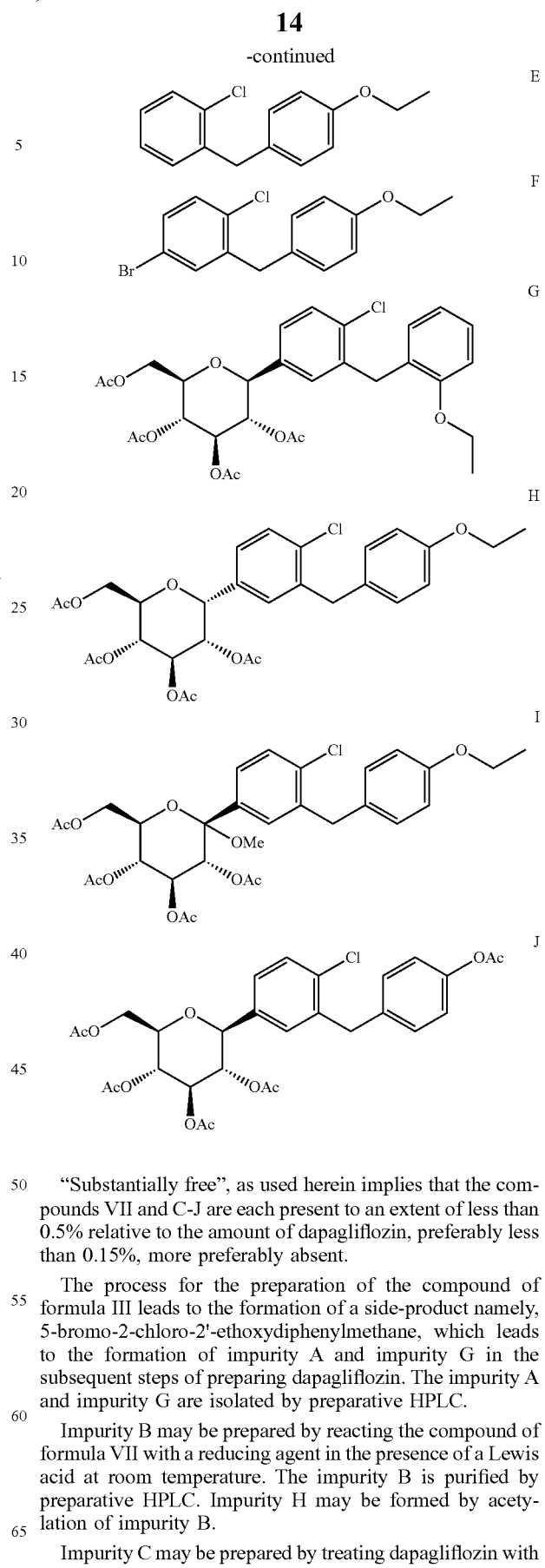

E

F

G

H

I

J

"Substantially free", as used herein implies that the compounds VII and C-J are each present to an extent of less than 0.5% relative to the amount of dapagliflozin, preferably less than 0.15%, more preferably absent.

The process for the preparation of the compound of formula III leads to the formation of a side-product namely, 5-bromo-2-chloro-2'-ethoxydiphenylmethane, which leads to the formation of impurity A and impurity G in the subsequent steps of preparing dapagliflozin. The impurity A and impurity G are isolated by preparative HPLC.

Impurity B may be prepared by reacting the compound of formula VII with a reducing agent in the presence of a Lewis acid at room temperature. The impurity B is purified by preparative HPLC. Impurity H may be formed by acetylation of impurity B.

Impurity C may be prepared by treating dapagliflozin with Lewis acid such as boron tribromide and the like.

Impurity D may be prepared by starting from 3-bromo-2-chlorobenzoic acid instead of 5-bromo-2-chlorobenzoic acid and by following similar steps as for preparation of dapagliflozin.

Impurity E may be prepared by reacting 2-chlorobenzoic acid with thionyl chloride to give 2-chlorobenzoyl chloride which on reaction with ethoxybenzene in presence of aluminium chloride gives impurity E.

Impurity I may be prepared by acetylation of the compound of the formula VII

Impurity J may be prepared by treatment of the compound of formula VIII with Lewis acid such as boron tribromide, followed by acetylation step to give impurity J.

In one embodiment, the present invention provides the compound of formula VIII substantially free of compounds E, F, G, H, I and J.

In one embodiment, the present invention provides dapagliflozin free of any of the below listed impurities K-M.

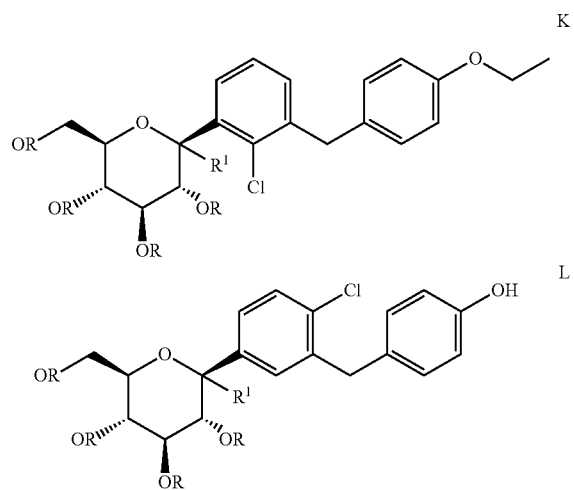

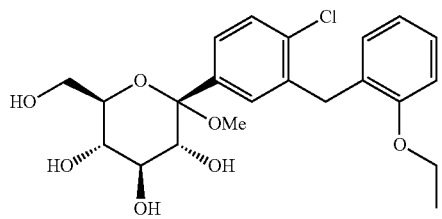

wherein in K and L, R=H, Ac; $R^1$=H, —$OCH_3$; and when R=H then $R^1$=-$OCH_3$ In one embodiment, the present invention provides a premix comprising dapagliflozin and a pharmaceutically acceptable carrier.

The pharmaceutically acceptable carrier may be selected from the group consisting of a cellulose derivative such as croscarmellose sodium, microcrystalline cellulose, hydroxyethylcellulose (HEC), hydroxypropylcellulose (HPC), hydroxypropylmethylcellulose (HPMC), hydroxymethylethylcellulose (HEMC), ethylcellulose (EC), methylcellulose (MC), cellulose esters, cellulose glycolate, hydroxypropyl methyl cellulose phthalate, polymethylacrylate (HPMCP), hypromellose; vinylpyrrolidone polymer such as polyvinylpyrrolidone and polyols such as mannitol, sorbitol and the like; sugars such as lactose.

In one embodiment, the present invention provides a process for the preparation of a premix comprising dapagliflozin and a pharmaceutically acceptable carrier selected from the group consisting of mannitol, microcrystalline cellulose, or mixtures thereof, the process comprising:
(a) dissolving dapagliflozin in a solvent;
(b) adding a pharmaceutically acceptable carrier to the solution prepared in step (a); and
(c) removing the solvent from the mixture obtained in step (b).

In one embodiment, the removal of solvent in step (c) may be performed by techniques known in the art. The techniques used may include vacuum evaporation, fluid bed drying, spray drying, freeze drying, vacuum drying, tray drying and the like.

In one embodiment, dissolution of dapagliflozin in the solvent may be carried out at a temperature of about 20° C. to about 30° C. If required, the dissolution may be performed under heating. The pharmaceutically acceptable carrier may then be added at a temperature of about 20° C. to about 30° C. and the reaction mixture may optionally be heated. The solvent may then be removed and optionally the residue may be degassed to obtain the premix.

In one embodiment, the present invention provides a premix of dapagliflozin and mannitol.

In one embodiment, the present invention provides a premix of dapagliflozin and microcrystalline cellulose.

Figure 2:
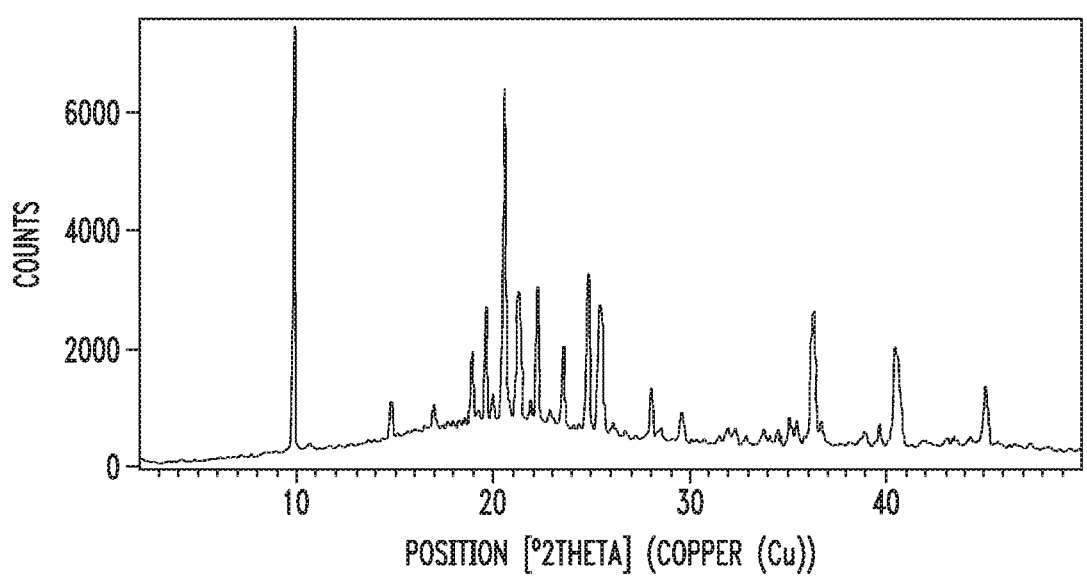
FIG. 2 is a characteristic XRPD of premix of dapagliflozin and mannitol as obtained in example 11.

In one embodiment, the present invention provides a premix of dapagliflozin and mannitol characterized by X-ray powder diffraction pattern which is substantially in accordance with FIG. 2.

Figure 3:
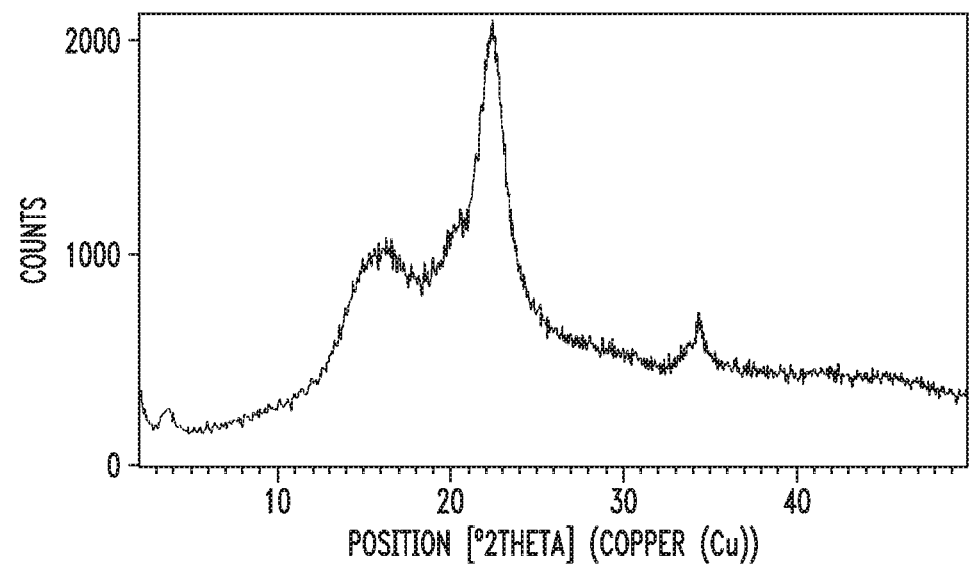
FIG. 3 is a characteristic XRPD of premix of dapagliflozin and microcrystalline cellulose as obtained in example 12.

In one embodiment, the present invention provides a premix of dapagliflozin and microcrystalline cellulose characterized by X-ray powder diffraction pattern which is substantially in accordance with FIG. 3.

In one embodiment, the present invention provides a premix of dapagliflozin with mannitol wherein, the premix contains substantially amorphous dapagliflozin.

In one embodiment, the present invention provides a premix of dapagliflozin with mannitol wherein, the premix contains substantially amorphous dapagliflozin in stable form.

In one embodiment, the present invention provides a premix of dapagliflozin with microcrystalline cellulose wherein, the premix contains substantially amorphous dapagliflozin.

In one embodiment, the present invention provides a premix of dapagliflozin with microcrystalline cellulose wherein, the premix contains substantially amorphous dapagliflozin in stable form.

As used herein, "substantially amorphous dapagliflozin" has less than about 50% crystalline dapagliflozin. In one embodiment, substantially amorphous dapagliflozin has less than about 30% crystalline dapagliflozin. In one embodiment, substantially amorphous dapagliflozin has less than about 20% crystalline dapagliflozin. Preferably, the substantially amorphous dapagliflozin has less than about 15% crystalline dapagliflozin.

As used herein, "substantially amorphous dapagliflozin in stable form" implies substantially amorphous dapagliflozin which is stable for a period of 6 months when kept under conditions of temperature of about 2° C. to about 8° C. and ambient temperature (about 20° C. to about 30° C.).

The present invention provides a crystalline 2,3-butanediol solvate of dapagliflozin characterized by an X-ray powder diffraction (XRPD) spectrum having peak reflections at about 3.7, 9.6, 14.7, 16.7 and 18.4±0.2 degrees 2 theta.

Figure 4:
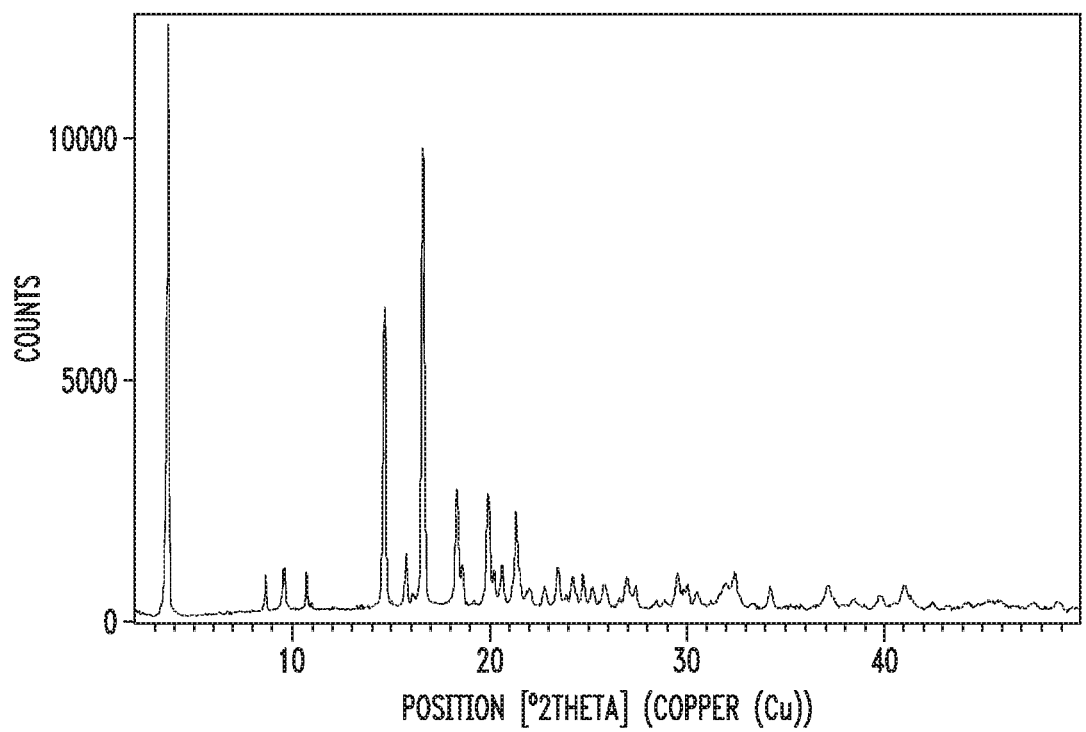
FIG. 4 is a characteristic XRPD of crystalline 2,3-butanediol solvate of dapagliflozin as obtained in Example 13.
Figure 5:
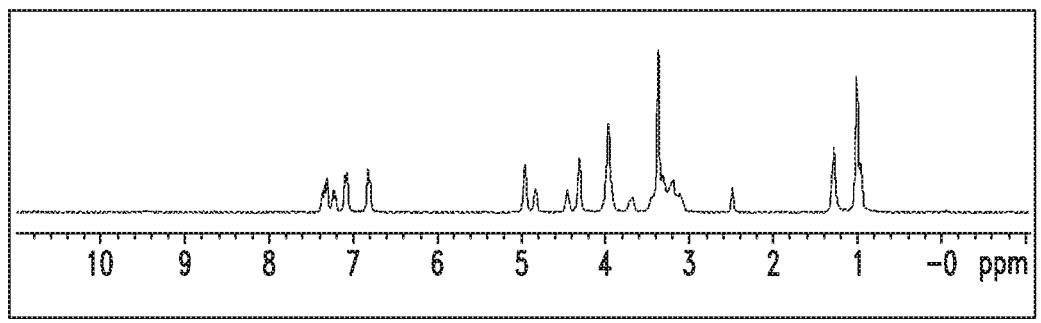
FIG. 5 is a proton NMR spectrum of crystalline 2,3-butanediol solvate of dapagliflozin as obtained in Example 13.
Figure 6:
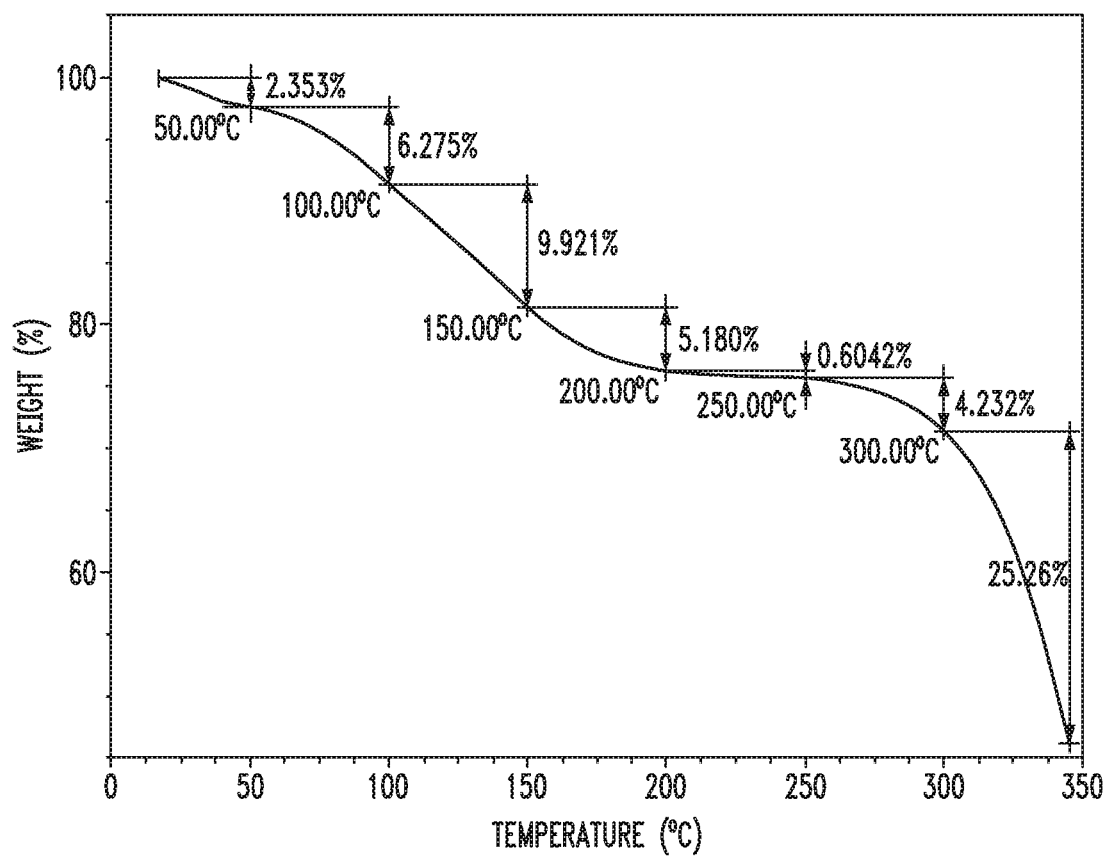
FIG. 6 is a TGA thermogram of crystalline 2,3-butanediol solvate of dapagliflozin as obtained in Example 13.
Figure 7:
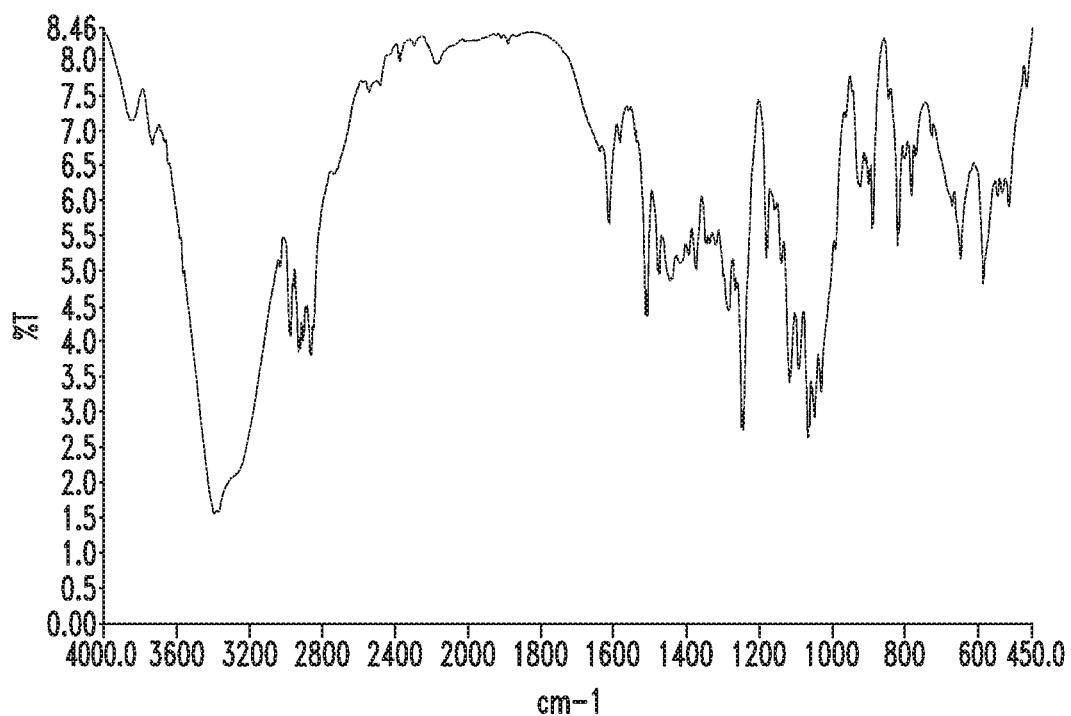
FIG. 7 is an IR spectrum of crystalline 2,3-butanediol solvate of dapagliflozin as obtained in Example 13.
Figure 8:
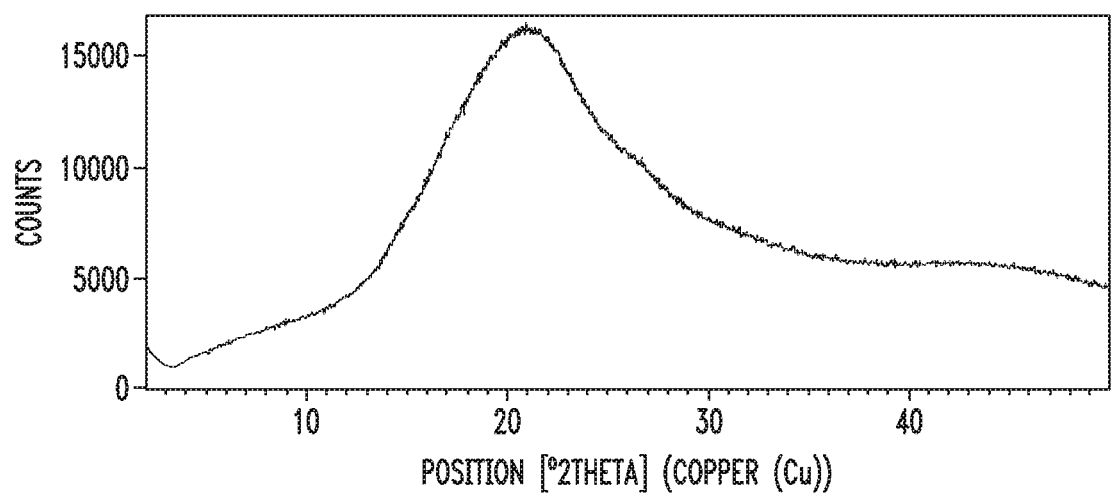
FIG. 8 is a characteristic XRPD of dapagliflozin in amorphous form as obtained in Example 35.

The present invention provides a crystalline 2,3-butanediol solvate of dapagliflozin characterized by an X-ray powder diffraction (XRPD) pattern as depicted in FIG. 1, a TGA thermogram as depicted in FIG. 3, an IR spectrum as depicted in FIG. 4.

In one embodiment, the present invention provides a crystalline 2,3-butanediol solvate of dapagliflozin characterized by TGA thermogram, showing a weight loss of about 18 weight % to 26 weight % up to 250° C. determined over the temperature range of 0° C. to 350° C. and heating rate 10° C./min.

In one embodiment, the present invention provides a crystalline 2,3-butanediol solvate of dapagliflozin characterized by TGA thermogram, showing a weight loss of about 18 weight % to 26 weight % up to 250° C. determined over the temperature range of 0° C. to 350° C. and heating rate 10° C./min which is in accordance with FIG. 3.

In one embodiment, the present invention provides a crystalline 2,3-butanediol monohydrate of dapagliflozin characterized by TGA thermogram, showing a weight loss of about 24.3 weight % up to 250° C. determined over the temperature range of 0° C. to 350° C. and heating rate 10° C./min which corresponds to one mole of water and one mole of butanediol per mole of structure analyzed.

In one embodiment, the crystalline 2,3-butanediol solvate of dapagliflozin is a mono-butanediol solvate of dapagliflozin (1:1 solvate).

In one embodiment, the crystalline 2,3-butanediol solvate of dapagliflozin is in the form of a hydrate.

In one embodiment, the crystalline 2,3-butanediol solvate of dapagliflozin is in the form of a monohydrate.

In one embodiment, the crystalline 2,3-butanediol solvate of dapagliflozin is in the form of a dihydrate.

In one embodiment, the present invention provides a crystalline 2,3-butanediol solvate of dapagliflozin characterized by a proton NMR spectrum having peak positions at 7.40-7.25 (m, 2H), 7.25-7.18 (d, 1H), 7.12-7.00 (d, 2H), 6.81-6.75 (d, 2H), 4.97 (brs, 2H), 4.84 (brs, 1H), 4.46 (brs, 1H), 4.32 (brs, 2H), 4.10-3.90 (m, 4H), 3.80-3.60 (m, 1H), 3.55-3.05 (m, 8H), 1.29 (t, 3H), 1.05-0.85 (m, 6H) ppm.

In one embodiment, the present invention provides a crystalline 2,3-butanediol solvate of dapagliflozin characterized by DSC thermogram having an endothermic peak at about 61±2° C.

In another embodiment, the present invention provides a process for the preparation of crystalline 2,3-butanediol solvate of dapagliflozin, the process comprising:
(a) treating dapagliflozin with 2,3-butanediol, optionally in the presence of a solvent, to form a solution;
(b) obtaining crystalline 2,3-butanediol solvate of dapagliflozin from the solution of step (a); and
(c) isolating the crystalline 2,3-butanediol solvate of dapagliflozin.

In (a) of the process for the preparation of crystalline 2,3-butanediol solvate of dapagliflozin, dapagliflozin is treated with 2,3-butanediol, optionally in the presence of a solvent, to form a solution.

The 2,3-butanediol used may be the (2R,3R)-enantiomer, or the (2S,3S)-enantiomer, or the meso compound (2R,3S) (or equivalently (2S,3R)), or the racemic compound. Preferably, racemic 2,3-butanediol is used.

The solvent includes but is not limited to haloalkanes such as dichloromethane, chloroform, ethylene dichloride, and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; ethers such as diethyl ether, diisopropyl ether, methyl tert-butyl ether, tetrahydrofuran, dioxane and the like; esters such as methyl acetate, ethyl acetate, n-propyl acetate, isopropyl acetate, butyl acetate, tert-butyl acetate and the like; hydrocarbons such as toluene, xylene, chlorobenzene, heptane, hexane, cyclohexane and the like; dimethyl sulfoxide; dimethyl formamide; dimethyl acetamide; water; or mixtures thereof.

The reaction may be carried out at a temperature in the range from about 20° C. to about 120° C. Preferably, the reaction is carried out at about 25° C. to about 80° C. The stirring time may range from about 30 minutes to about 10 hours, or longer. The solution may be optionally treated with charcoal and filtered to get a particle-free solution.

In (b) of the process for the preparation of crystalline 2,3-butanediol solvate of dapagliflozin, crystalline 2,3-butanediol solvate of dapagliflozin is obtained from the solution of step (a).

In one embodiment, the step (b) of obtaining crystalline 2,3-butanediol solvate of dapagliflozin comprises:
(i) optionally cooling and stirring the solution obtained in (a); or
(ii) removing the solvent from the solution obtained in (a); or
(iii) treating the solution of step (a) with an anti-solvent to form a mixture and optionally, cooling and stirring the obtained mixture.

In (i) of the above process, crystalline 2,3-butanediol solvate of dapagliflozin is obtained by optionally cooling and stirring the solution obtained in step (a). The stirring time may range from about 30 minutes to about 10 hours, or longer. The temperature may range from about 0° C. to about 90° C.

In (ii) of the above process, crystalline 2,3-butanediol solvate of dapagliflozin is obtained by removing the solvent from the solution obtained in step (a). Removal of solvent may be accomplished by substantially complete evaporation of the solvent or concentrating the solution, cooling the solution if required and filtering the obtained solid. The solution may be completely evaporated in, for example, a rotavapor, a vacuum paddle dryer or in a conventional reactor under vacuum above about 720 mm Hg, or evaporated by lyophilisation, freeze-drying technique, spray drying, fluid bed drying, flash drying, spin flash drying, thin-film drying. The solution may also be completely evaporated as discussed supra, adding a second solvent, optionally cooling and stirring the obtained mixture and filtering the obtained solid.

The second solvent includes but is not limited to haloalkanes such as dichloromethane, chloroform, ethylene dichloride, and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; ethers such as diethyl ether, diisopropyl ether, methyl tert-butyl ether, tetrahydrofuran, dioxane and the like; esters such as methyl acetate, ethyl acetate, n-propyl acetate, isopropyl acetate, butyl acetate, tert-butyl acetate and the like; hydrocarbons such as toluene, xylene, chlorobenzene, heptane, hexane, cyclohexane and the like; dimethyl sulfoxide; dimethyl formamide; dimethyl acetamide; water; or mixtures thereof.

In (iii) of the above process, crystalline 2,3-butanediol solvate of dapagliflozin is obtained by adding an anti-solvent to the solution obtained in step (a) to form a mixture and optionally, cooling and stirring the obtained mixture. The stirring time may range from about 30 minutes to about 10 hours, or longer. The temperature may range from about 0° C. to about 90° C.

The anti-solvent is selected such that crystalline 2,3-butanediol solvate dapagliflozin is precipitated out from the solution.

The anti-solvent includes but is not limited to haloalkanes such as dichloromethane, chloroform, ethylene dichloride, and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; ethers such as diethyl ether, diisopropyl ether, methyl tert-butyl ether, tetrahydrofuran, dioxane and the like; esters such as methyl acetate, ethyl acetate, n-propyl acetate, isopropyl acetate, butyl acetate, tert-butyl acetate and the like; hydrocarbons such as toluene, xylene, chlorobenzene, heptane, hexane, cyclohexane and the like; dimethyl sulfoxide; dimethyl formamide; dimethyl acetamide; water; or mixtures thereof.

In (c) of the process for the preparation of crystalline 2,3-butanediol solvate of dapagliflozin, the crystalline 2,3-butanediol solvate of dapagliflozin is isolated by any method known in the art. The method, may involve any of techniques, known in the art, including filtration by gravity or by suction, centrifugation, and the like.

In one embodiment, the crystalline 2,3-butanediol solvate of dapagliflozin obtained by the above process is a mono-butanediol solvate of dapagliflozin (1:1 solvate).

In one embodiment, the crystalline 2,3-butanediol solvate of dapagliflozin obtained by the above process is in the form of a hydrate.

In one embodiment, the crystalline 2,3-butanediol solvate of dapagliflozin obtained by the above process is in the form of a monohydrate.

In one embodiment, the crystalline 2,3-butanediol solvate of dapagliflozin obtained by the above process is in the form of a dihydrate.

In one embodiment, the present invention provides a process for the preparation of crystalline 2,3-butanediol solvate of dapagliflozin, the process comprising:
(a) reacting D-glucitol, 1,5-anhydro-1-C-[4-chloro-3-[(4-ethoxyphenyl)methyl] phenyl]-, 2,3,4,6-tetraacetate, (1S)- with a base in the presence of a solvent to give dapagliflozin;
(b) treating dapagliflozin with 2,3-butanediol, optionally in the presence of a solvent, to form a solution;
(c) obtaining crystalline 2,3-butanediol solvate of dapagliflozin from the solution of step (b); and
(d) isolating the crystalline 2,3-butanediol solvate of dapagliflozin.

In (a) of the process for the preparation of crystalline 2,3-butanediol solvate of dapagliflozin, D-glucitol, 1,5-anhydro-1-C-[4-chloro-3-[(4-ethoxyphenyl)methyl] phenyl]-, 2,3,4,6-tetraacetate, (1S)- is reacted with a base in the presence of a solvent to give dapagliflozin.

The suitable base includes, but is not limited to alkali metal hydroxides such as lithium hydroxide, sodium hydroxide, potassium hydroxide; alkaline earth metal hydroxides; alkali metal hydrides such as sodium hydride, potassium hydride; alkali metal alcoholates such as lithium methoxide, sodium methoxide, potassium methoxide, sodium ethoxide, potassium ethoxide, potassium tert-butoxide; alkaline earth metal alcoholates such as calcium ethoxide, magnesium iso-propoxide. Preferably the base selected is sodium hydroxide.

In (b) of the process for the preparation of crystalline 2,3-butanediol solvate of dapagliflozin, dapagliflozin is treated with 2,3-butanediol, optionally in the presence of a solvent, to form a solution.

The process steps (b), (c) and (d) are as discussed supra.

In one embodiment, the dapagliflozin obtained in step (a) is isolated and then treated with 2,3-butanediol.

In one embodiment, the dapagliflozin obtained in step (a) is in-situ treated with 2,3-butanediol.

The present invention provides a process for the preparation of dapagliflozin in amorphous form, the process comprising:
(a) dissolving 2,3-butanediol solvate of dapagliflozin in a solvent to form a solution; and
(b) recovering dapagliflozin in amorphous form from the solution of step (a).

In (a) of the process for the preparation of dapagliflozin in amorphous form, 2,3-butanediol solvate of dapagliflozin is dissolved in a solvent to form a solution.

The solvent used for dissolution of 2,3-butanediol solvate of dapagliflozin includes but is not limited to haloalkanes such as dichloromethane, chloroform, ethylene dichloride, and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; ethers such as diethyl ether, diisopropyl ether, methyl tert-butyl ether, tetrahydrofuran, dioxane and the like; esters such as methyl acetate, ethyl acetate, n-propyl acetate, isopropyl acetate, tert-butyl acetate and the like; hydrocarbons such as toluene, xylene, chlorobenzene, heptane, hexane and the like; dimethyl sulfoxide; dimethyl formamide; dimethyl acetamide; water; or mixtures thereof.

Suitable temperature for dissolution of 2,3-butanediol solvate of dapagliflozin in a solvent may range from about 0° C. to about the reflux temperature of the solvent. Stirring may be continued for any desired time period to achieve a complete dissolution of the compound. The stirring time may range from about 30 minutes to about 1 hour, or longer. The solution may be optionally treated with charcoal and filtered to get a particle-free solution.

In (b) of the process for the preparation of dapagliflozin in amorphous form, dapagliflozin in amorphous form is recovered from the solution of step (a).

In one embodiment, dapagliflozin in amorphous form is recovered by removing the solvent from the solution obtained in step (a). Removal of solvent may be accomplished by substantially complete evaporation of the solvent or concentrating the solution, cooling the solution if required and filtering the obtained solid. The solution may also be completely evaporated in, for example, a rotavapor, a vacuum paddle dryer or in a conventional reactor under vacuum above about 720 mm Hg, or evaporated by lyophilisation, freeze-drying technique, spray drying, fluid bed drying, flash drying, spin flash drying, thin-film drying, agitated nutsche filter dryer.

In one embodiment, dapagliflozin in amorphous form is recovered by adding an anti-solvent to the solution obtained in step (a) to form a mixture and optionally, cooling and stirring the obtained mixture. The stirring time may range from about 30 minutes to about 10 hours, or longer. The temperature may range from about 0° C. to about 30° C.

The anti-solvent is selected such that dapagliflozin in amorphous form is precipitated out from the solution.

The anti-solvent includes but is not limited to esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; haloalkanes such as dichloromethane, chloroform, ethylene dichloride, and the like; dimethyl formamide; dimethyl sulfoxide; dimethyl acetamide; water; or mixtures thereof.

The present invention provides use of 2,3-butanediol solvate of dapagliflozin in the preparation of amorphous dapagliflozin.

In one embodiment, the present invention provides a process for the preparation of amorphous dapagliflozin, the process comprising:
(a) dissolving dapagliflozin, or solvate thereof, in a suitable solvent to form a solution;
(b) obtaining amorphous dapagliflozin from the solution of step (a); and
(c) isolating the amorphous dapagliflozin.

In (a) of the process for the preparation of amorphous dapagliflozin, dapagliflozin or solvate thereof, is dissolved in a suitable solvent to form a solution.

The solvate of dapagliflozin includes solvate with water, methanol, ethanol, n-propanol, isopropanol, n-butanol, isobutanol, tert-butanol, ethylene glycol, butanediol, ethyl acetate, n-butyl acetate, isobutyl acetate, acetonitrile, acetone, butanone, methyl isobutyl ketone, tetrahydrofuran, 2-methyl tetrahydrofuran, dioxane, chloroform, dichloromethane, hexane, n-heptane, toluene, N-methyl pyrrolidone, dimethyl formamide or dimethyl sulfoxide.

The solvent used for dissolution of solvate of dapagliflozin is as discussed supra for dissolution of 2,3-butanediol solvate of dapagliflozin.

In (b) of the process for the preparation of amorphous dapagliflozin, amorphous dapagliflozin is obtained from the solution of step (a).

In one embodiment, the amorphous dapagliflozin is obtained by removing the solvent from the solution obtained in (a). Removal of solvent may be accomplished as discussed supra.

In one embodiment, the amorphous dapagliflozin is obtained by adding an anti-solvent to the solution obtained in (a) to form a mixture and optionally, cooling and stirring the obtained mixture. The anti-solvent is selected such that amorphous dapagliflozin is precipitated out from the solution. The anti-solvent is as discussed supra.

In (c) of the process for the preparation of amorphous dapagliflozin, the amorphous dapagliflozin is isolated by any method known in the art. The method, may involve any of techniques, known in the art, including filtration by gravity or by suction, centrifugation, and the like.

The present invention provides dapagliflozin in substantially amorphous form.

In one embodiment, the present invention provides amorphous dapagliflozin in a purity of about 99.9% w/w, as determined by HPLC.

The present invention provides amorphous dapagliflozin in stable form.

In one embodiment, the present invention provides pure amorphous dapagliflozin in stable form.

In one preferred embodiment, the present invention provides pure amorphous dapagliflozin in stable form with a purity of about 99.9% w/w, as determined by HPLC.

In one embodiment, the present invention provides a process for the preparation of solvates of dapagliflozin, the process comprising:
(a) dissolving dapagliflozin in a suitable solvent, optionally in presence of additional solvent, to form a solution;
(b) obtaining solvate of dapagliflozin from the solution of step (a); and
(c) isolating the solvate of dapagliflozin.

The solvate of dapagliflozin includes solvate with water, methanol, ethanol, n-propanol, isopropanol, n-butanol, isobutanol, tert-butanol, ethylene glycol, butanediol, ethyl acetate, n-butyl acetate, isobutyl acetate, acetonitrile, acetone, butanone, methyl isobutyl ketone, tetrahydrofuran, 2-methyl tetrahydrofuran, dioxane, chloroform, dichloromethane, hexane, n-heptane, toluene, N-methyl pyrrolidone, dimethyl formamide or dimethyl sulfoxide.

The solvent used for dissolution of dapagliflozin is as discussed supra.

The additional solvent includes but is not limited to esters such as methyl acetate, ethyl acetate, n-propyl acetate, isopropyl acetate, tert-butyl acetate and the like; hydrocarbons such as toluene, xylene, chlorobenzene, heptane, hexane and the like; ethers such as diethyl ether, diisopropyl ether, methyl tert-butyl ether, tetrahydrofuran, dioxane and the like; ketones such as acetone, ethyl methyl ketone, methyl isobutyl ketone and the like; alcohols such as methanol, ethanol, 1-propanol, 2-propanol, 1-butanol, 2-butanol, 1-pentanol, 1-octanol and the like; haloalkanes such as dichloromethane, chloroform, ethylene dichloride, and the like; dimethyl formamide; dimethyl sulfoxide; dimethyl acetamide; water; or mixtures thereof.

In (b) of the process for the preparation of solvate of dapagliflozin, the solvate of dapagliflozin is obtained from the solution of step (a), the process comprising:
(i) optionally cooling and stirring the solution obtained in (a); or
(ii) removing the solvent from the solution obtained in (a); or
(iii) treating the solution of step (a) with an anti-solvent to form a mixture and optionally, cooling and stirring the obtained mixture.

The anti-solvent is selected such that the solvate of dapagliflozin is precipitated out from the solution. The anti-solvent is as discussed supra for 2,3-butanediol solvate dapagliflozin.

In one embodiment, the present invention provides pharmaceutical compositions comprising dapagliflozin or solvate thereof obtained by the processes herein described, having a $D_{50}$ and $D_{90}$ particle size of less than about 150 microns, preferably less than about 100 microns, more preferably less than about 50 microns, still more preferably less than about 20 microns, still more preferably less than about 15 microns and most preferably less than about 10 microns. The particle size disclosed here can be obtained by, for example, any milling, grinding, micronizing or other particle size reduction method known in the art to bring the solid state dapagliflozin or solvate thereof into any of the foregoing desired particle size range.

In one embodiment, the present invention provides pharmaceutical composition/formulation comprising crystalline 2,3-butanediol solvate of dapaglifozin and at least one pharmaceutically acceptable carrier.

The pharmaceutically acceptable carrier may comprise bulking agents such as microcrystalline cellulose, lactose, or the like; binders such as pregelatinized starch, or the like; disintegrants such as sodium starch glycolate, crospovidone, croscarmellose sodium, or the like; glidants such as silicon dioxide, talc, or the like; lubricants such as magnesium stearate, or the like; as well as others known in the art.

In one embodiment, the crystalline 2,3-butanediol solvate of dapagliflozin formulation is in a form selected from the group consisting of a tablet, a stock granulation, and a capsule.

In one embodiment, the present invention provides a method for treating or delaying the progression or onset of Type I and Type II diabetes, impaired glucose tolerance, insulin resistance, nephropathy, retinopathy, neuropathy, cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis, hypertension, or Syndrome X (Metabolic Syndrome) comprising administering to a mammalian subject or patient in need of such treatment a therapeutically effective amount of an immediate release pharmaceutical formulation comprising crystalline 2,3-butanediol solvate of dapagliflozin and a pharmaceutically acceptable carrier.

The examples that follow are provided to enable one skilled in the art to practice the invention and are merely illustrative of the invention. The examples should not be read as limiting the scope of the invention as defined in the features and advantages.

EXAMPLES

Example 1: Preparation of 5-bromo-2-chlorobenzoyl Chloride

To a suspension of 5-promo-2-chlorobenzoic acid (10 g) in methylene dichloride (40 mL), dimethylformamide (0.2 g) and thionyl chloride were added and the reaction mixture was refluxed for about 2 h. After completion of reaction, the solvent was distilled out. The mass obtained was degassed under vacuum followed by stripping with cyclohexane to give crude 5-bromo-2-chlorobenzoyl chloride (10.8 g).

Example 2: Preparation of 5-bromo-2-chloro-4'-ethoxybenzophenone (Compound of Formula II)

5-bromo-2-chlorobenzoyl chloride (10.7 g) was dissolved in methylene dichloride (40 mL) and the reaction mixture was cooled to about −8° C. to about −12° C. under inert atmosphere. Aluminum chloride (5.65 g) was added to the reaction mixture followed by addition of a solution of ethoxybenzene in methylene dichloride. The reaction mixture was stirred for about 1 h at about −8° C. to −12° C. and then quenched in dilute hydrochloric acid followed by extraction with methylene dichloride. The organic layer was washed with sodium bicarbonate solution and concentrated. The residue obtained was crystallized from methanol to give 5-bromo-2-chloro-4'-ethoxybenzophenone (8.5 g). HPLC purity: 99.34%

Example 3: Preparation of 5-bromo-2-chloro-4'-ethoxydiphenylmethane (Compound of Formula III)

To a mixture of 5-bromo-2-chloro-4'-ethoxybenzophenone (10 g) and methylene dichloride (50 mL), cooled to about 0° C. to about 5° C., triethylsilane (11.98 g) and titanium chloride (22.3 g) were added. The reaction mixture was stirred for about 3 h at about 10° C. to about 15° C. The reaction mixture was quenched into chilled water. The organic layer was separated, washed with water and sodium bicarbonate solution and concentrated under vacuum followed by stripping with toluene. The residue obtained was stirred with methanol, filtered and dried to give 5-bromo-2-chloro-4'-ethoxydiphenylmethane (9 g). HPLC purity: 99.4%

Example 4: Preparation of 2,3,4,6-tetra-O-(trimethylsilyl)-D-glucono-1,5-lactone (Compound of Formula V)

To a mixture of D-glucono-1,5-lactone (10 g) and iodine (0.28 g) in methylene dichloride (80 mL), hexamethyldisilazane (36.1 g) was added and the reaction mixture was refluxed. After completion of reaction, the reaction mixture was concentrated and degassed to give 2,3,4,6-tetra-O-(trimethylsilyl)-D-glucono-1,5-lactone as liquid (25 g). HPLC purity: 95%

Example 5: Preparation of D-glucopyranoside, methyl 1-C-[4-chloro-3-[(4-ethoxyphenyl)methyl]phenyl] (Compound of Formula VII Wherein R is Methyl)

To a mixture of 2,3,4,6-tetra-O-(trimethylsilyl)-D-glucono-1,5-lactone (25 g) and 5-bromo-2-chloro-4'-ethoxydiphenylmethane (8.7 g) in tetrahydrofuran (174 mL), cooled to about −75° C. to about −88° C. under nitrogen atmosphere, n-butyl lithium in hexane (50 mL) was slowly added. The reaction mixture was stirred at about the same temperature and then mixture of methanol and methanesulphonic acid was added to it. The reaction mixture was quenched into sodium bicarbonate solution and extracted with ethyl acetate. The organic layer was separated, washed with saturated sodium chloride solution and concentrated under vacuum to obtain a residue. The residue was purified with a mixture of toluene and cyclohexane. Yield: 11 g as thick mass with 80-85% HPLC purity.

Example 6: Preparation of D-glucitol, 1,5-anhydro-1-C-[4-chloro-3-[(4-ethoxyphenyl) methyl]phenyl]

To a mixture of D-glucopyranoside, methyl 1-C-[4-chloro-3-[(4-ethoxyphenyl)methyl]phenyl] in methylene dichloride (40 mL) and acetonitrile (40 mL), cooled to about −40° C. to about −45° C., triethylsilane (8.74 g) was added followed by addition of boron trifluoride etherate (10.67 g) maintaining the temperature at about −40° C. to about −45° C. The reaction mixture was quenched in sodium bicarbonate solution and extracted with ethyl acetate. The organic layer was separated, concentrated and degassed under vacuum to give title compound (11 g) as thick residue with 80-85% HPLC purity.

Example 7: Preparation of D-Glucitol, 1,5-anhydro-1-C-[4-chloro-3-[(4-ethoxyphenyl)methyl]phenyl]-, 2,3,4,6-tetraacetate, (1S)-

To a cooled solution of D-glucitol, 1,5-anhydro-1-C-[4-chloro-3-[(4-ethoxyphenyl) methyl]phenyl]-(11 g) in methylene dichloride (55 mL) at about 0° C. to about 5° C., diisopropylethylamine, dimethylaminopyridine and acetic anhydride were added and the reaction mixture was stirred. After completion of reaction, the reaction mixture was quenched by adding water. The aqueous layer was separated and extracted with methylene dichloride. The organic layer was separated, washed with sodium bicarbonate solution and concentrated under vacuum to obtain residue which was stripped out with methanol. The residue was purified with methanol and charcoal, followed by diisopropyl ether and methanol crystallization. Yield: 10 g, HPLC purity: 99.6%

Example 8: Preparation of D-glucitol, 1,5-anhydro-1-C-[4-chloro-3-[(4-ethoxyphenyl)methyl]phenyl] (Dapagliflozin)

To a stirred solution of D-glucitol, 1,5-anhydro-1-C-[4-chloro-3-[(4-ethoxyphenyl)methyl]phenyl]-, 2,3,4,6-tetraacetate, (1S)-, (10 g) in THF:methanol:water mixture (50 mL:50 mL:30 mL), sodium hydroxide was added and the reaction mixture was stirred. After completion of reaction, the solvents were distilled out under vacuum and the residue obtained was dissolved in methylene dichloride and washed with water and brine and dried over sodium sulfate. The reaction mixture was concentrated and degassed to give off-white to white solids of D-glucitol, 1,5-anhydro-1-C[4-chloro-3-[(4-ethoxyphenyl)methyl]phenyl]-(dapagliflozin) Yield: 7 g (XRD matches with amorphous form) HPLC purity: 99.8%

Example 9: Preparation of D-glucitol, 1,5-anhydro-1-C-[4-chloro-3-[(4-ethoxyphenyl)methyl]phenyl]-, (1S), Compounded with (2S)-propane-1,2-diol (1:1) monohydrate To D-glucitol, 1,5-anhydro-1-C[4-chloro-3-[(4-ethoxyphenyl)methyl]phenyl]-(7 g) in isopropyl acetate cooled to about 0° C. to about 5° C., was added (S)-1,2-propanediol and water and the reaction mixture was stirred. The solid obtained was filtered and dried to give title compound (6.3 g) with 99.7% HPLC purity.

Example 10: Preparation of D-Glucitol, 1,5-anhydro-1-C-[4-chloro-3-[(4-ethoxyphenyl)methyl]phenyl]-, 2,3,4,6-tetraacetate, (1S)- from D-glucono-1,5-lactone (One-Pot Synthesis)

To a mixture of D-glucono-1,5-lactone (10 g) in methylene dichloride (80 mL), hexamethyldisilazane (36.1 g) was added and the reaction mixture was refluxed. After completion of reaction, the reaction mixture was concentrated and degassed. The residue obtained was dissolved in tetrahydrofuran. 5-Bromo-2-chloro-4'-ethoxydiphenylmethane (8.7 g) was added to the reaction mixture which was cooled to about −75° C. to about −85° C. under nitrogen atmosphere. n-Butyl lithium in hexane (50 mL) was slowly added to the reaction mixture maintaining the temperature between −75° C. to about −85° C. The reaction mixture was stirred at about the same temperature and then mixture of methanol and methanesulphonic acid was added to it. The reaction mixture was quenched into sodium bicarbonate solution and extracted with ethyl acetate. The organic layer was separated, washed with saturated sodium chloride solution and concentrated under vacuum to obtain a residue. This residue was purified by a mixture of toluene and cyclohexane. To the product obtained, methylene dichloride and acetonitrile were added and the reaction mixture was cooled to about −40° C. to about −45° C. Triethylsilane (8.74 g) was added to the reaction mixture followed by addition of boron trifluoride etherate (10.67 g) maintaining temperature at about −40° C. to about −45° C. The reaction mixture was quenched in sodium bicarbonate solution. The aqueous layer was separated and extracted with ethyl acetate. The organic layer was separated, concentrated and degassed under vacuum. The thick residue obtained was dissolved in methylene dichloride and cooled to about 0° C. to about 5° C. Diisopropylethylamine, dimethylaminopyridine and acetic anhydride were added to the reaction mixture which was stirred. After completion of reaction, the reaction mixture was quenched by adding water. The aqueous layer was separated and extracted with methylene dichloride. The organic layer was separated, washed with sodium bicarbonate solution and concentrated under vacuum to obtain residue which was stripped out with methanol. The residue obtained was recrystallized with methanol and charcoal to give title compound (10 g) with 99.7% HPLC purity.

Example 11: Preparation of Dapagliflozin-Mannitol Premix

To a stirred mixture of dapagliflozin amorphous form (5 g) and methylene dichloride (25 mL), mannitol (5 g) was added and the reaction mixture was stirred. The reaction mixture was concentrated under reduced pressure and degassed. To the obtained residue, cyclohexane was added and the reaction mixture was stirred. The solid obtained was filtered, washed with cyclohexane and dried under vacuum to give title compound (9.8 g) with 99.74% HPLC purity. (XRD as per FIG. 2)

Example 12: Preparation of Dapagliflozin-Microcrystalline Cellulose Premix

To a stirred mixture of dapagliflozin amorphous form (5 g) and methylene dichloride (25 mL), microcrystalline cellulose (5 g) was added and the reaction mixture was stirred. The reaction mass was concentrated under reduced pressure and degassed. To the obtained residue, cyclohexane was added and the reaction mixture was stirred. The solid obtained was filtered, washed with cyclohexane and dried under vacuum to give title compound (9.4 g) with 99.57% HPLC purity. (XRD as per FIG. 3)

Example 13: Preparation of 2,3-Butanediol Solvate of Dapagliflozin

Dapagliflozin (2 g) was dissolved in ethyl acetate (10 mL) and 2,3-butanediol (0.463 g) and water (0.13 g) were added to it. The reaction mixture was concentrated and cyclohexane (30 mL) was added to it. The reaction mixture was stirred overnight. The solid obtained was filtered and dried. Yield: 1.8 g $^1$H NMR (300 MHz in DMSO-$d_6$): δ 7.40-7.25 (m, 2H), 7.25-7.18 (d, 1H), 7.12-7.00 (d, 2H), 6.81-6.75 (d, 2H), 4.97 (brs, 2H), 4.84 (brs, 1H), 4.46 (brs, 1H), 4.32 (brs, 2H), 4.10-3.90 (m, 4H), 3.80-3.60 (m, 1H), 3.55-3.05 (m, 8H), 1.29 (t, 3H), 1.05-0.85 (m, 6H) $^1$H NMR (300 MHz in DMSO-$d_6$+$D_2O$): 7.40-7.25 (m, 2H), 7.25-7.18 (d, 1H), 7.12-7.00 (d, 2H), 6.81-6.75 (d, 2H), 4.10-3.90 (m, 4H), 3.80-3.60 (m, 1H), 3.55-3.05 (m, 8H), 1.29 (t, 3H), 1.05-0.85 (m, 6H)

TGA analysis of 2,3-butanediol solvate of dapagliflozin: 24.3% weight loss up to 250° C. corresponds to one mole of water and one mole of butanediol per mole of structure analyzed.

Water content: 2.92%

XRPD peaks of 2,3-butanediol solvate of dapagliflozin:

| Pos. [°2Th.] | d-spacing [Å] | Rel. Int. [%] |
|---|---|---|
| 2.11 | 41.77 | 0.45 |
| 3.69 | 23.91 | 100.00 |
| 8.65 | 10.21 | 6.13 |
| 9.56 | 9.24 | 7.14 |
| 10.72 | 8.24 | 6.31 |
| 14.60 | 6.03 | 50.84 |
| 15.78 | 5.61 | 8.65 |
| 16.10 | 5.50 | 2.09 |
| 16.63 | 5.33 | 77.16 |
| 18.34 | 4.83 | 19.62 |
| 18.62 | 4.76 | 6.49 |
| 19.97 | 4.44 | 16.57 |
| 20.20 | 4.39 | 5.96 |
| 20.64 | 4.30 | 6.23 |
| 21.34 | 4.16 | 16.12 |
| 22.04 | 4.03 | 2.66 |
| 22.79 | 3.90 | 2.90 |
| 23.47 | 3.78 | 6.38 |
| 24.20 | 3.67 | 4.77 |
| 24.73 | 3.59 | 5.27 |
| 25.22 | 3.53 | 3.13 |
| 25.81 | 3.45 | 3.75 |
| 26.96 | 3.30 | 5.04 |
| 27.39 | 3.25 | 3.74 |
| 28.44 | 3.13 | 1.13 |
| 28.92 | 3.08 | 1.09 |
| 29.54 | 3.02 | 5.60 |
| 30.02 | 2.97 | 3.80 |
| 30.49 | 2.93 | 2.53 |
| 31.99 | 2.79 | 4.12 |
| 32.46 | 2.75 | 5.45 |
| 33.30 | 2.68 | 0.91 |
| 34.21 | 2.62 | 3.29 |
| 37.22 | 2.41 | 3.63 |
| 38.43 | 2.34 | 1.45 |
| 39.81 | 2.26 | 2.13 |
| 40.97 | 2.20 | 3.65 |
| 42.49 | 2.12 | 0.92 |
| 43.23 | 2.09 | 0.49 |

The following examples follow similar process as described in EXAMPLE 13 for preparation of 2,3-butanediol solvate of dapagliflozin wherein ethyl acetate (first solvent) and cyclohexane (second solvent) are replaced by below combinations.

| EXAMPLE No. | First Solvent | Second Solvent |
|---|---|---|
| EXAMPLE 14 | isopropyl acetate | cyclohexane |
| EXAMPLE 15 | methyl acetate | cyclohexane |
| EXAMPLE 16 | methylene chloride | cyclohexane |
| EXAMPLE 17 | ethylene dichloride | cyclohexane |
| EXAMPLE 18 | butyl acetate | cyclohexane |
| EXAMPLE 19 | isopropyl acetate | hexane |
| EXAMPLE 20 | ethyl acetate | hexane |
| EXAMPLE 21 | methyl acetate | hexane |
| EXAMPLE 22 | butyl acetate | hexane |

Example 23: Preparation of 2,3-Butanediol Solvate of Dapagliflozin

Dapagliflozin (2 g) was dissolved in ethyl acetate (10 mL) and 2,3-butanediol (0.463 g) and water (0.13 g) were added to it. The reaction mixture was stirred for about 30 min. Cyclohexane was added to the reaction mixture which was stirred overnight. The solid obtained was filtered and dried.

The following examples follow similar process as described in EXAMPLE 23 for preparation of 2,3-butanediol solvate of dapagliflozin wherein ethyl acetate (first solvent) and cyclohexane (second solvent) are replaced by below combinations.

| EXAMPLE No. | First Solvent | Second Solvent |
|---|---|---|
| EXAMPLE 24 | methyl acetate | cyclohexane |
| EXAMPLE 25 | isopropyl acetate | cyclohexane |
| EXAMPLE 26 | butyl acetate | cyclohexane |
| EXAMPLE 27 | methylene chloride | cyclohexane |
| EXAMPLE 28 | ethylene dichloride | cyclohexane |
| EXAMPLE 29 | ethyl acetate | hexane |
| EXAMPLE 30 | methyl acetate | hexane |
| EXAMPLE 31 | isopropyl acetate | hexane |
| EXAMPLE 32 | butyl acetate | hexane |
| EXAMPLE 33 | methylene chloride | hexane |
| EXAMPLE 34 | ethylene dichloride | hexane |

Example 35: Preparation of Amorphous Dapagliflozin

To a stirred solution of 2,3-butanediol solvate of dapagliflozin (2 g) in ethyl acetate, water was added and stirred for about 30 min. The two layers were separated and the organic layer was concentrated under reduced pressure. Isopropyl alcohol was added to the obtained residue and the reaction mixture was concentrated under reduced pressure and degassed for about 4 h to give amorphous dapagliflozin.

Example 36: Preparation of Amorphous Dapagliflozin

To a stirred solution of 2,3-butanediol solvate of dapagliflozin (2 g) in methylene dichloride, water was added and the reaction mixture was stirred for about 30 min. The two layers were separated and the organic layer was concentrated under reduced pressure. Isopropyl alcohol was added to the obtained residue and the reaction mixture was concentrated under reduced pressure and degassed for about 4 h to give amorphous dapagliflozin.

Example 37: Preparation of Amorphous Dapagliflozin

To a stirred solution of D-glucitol, 1,5-anhydro-1-C-[4-chloro-3-[(4-ethoxyphenyl)methyl]phenyl]-, 2,3,4,6-tetraacetate, (1S)-, in tetrahydrofuran: methanol: water mixture, was added sodium hydroxide and the reaction mixture was stirred for about 6 h. The reaction mixture was concentrated to give a residue and ethyl acetate and water were added it. The two layers were separated and the organic layer was concentrated and degassed to give amorphous dapagliflozin.

Example 38: Preparation of Dapagliflozin

To a stirred solution of D-glucitol, 1,5-anhydro-1-C-[4-chloro-3-[(4-ethoxyphenyl)methyl]phenyl]-, 2,3,4,6-tetraacetate, (1,9-, (10 g) in tetrahydrofuran:methanol:water mixture, was added sodium hydroxide and the reaction mixture was stirred. The reaction mixture was concentrated to give a residue and methylene dichloride and water were added it. The two layers were separated and the organic layer was concentrated and isopropyl alcohol was added to it. The reaction mixture was concentrated and degassed to give dapagliflozin. Yield: 7 g Isopropyl alcohol content: 3.5%
HPLC purity: 99.8%

Example 39: Preparation of 5-bromo-2-chloro-4'-ethoxydiphenylmethane

To a stirred mixture of 5-bromo-2-chloro-4'-ethoxybenzophenone (10 g), methylene dichloride (40 mL), acetonitrile (40 mL) and triethylsilane (13.69 g) was added boron trifluoride (14.6 g) at about 20° C. to about 50° C. The reaction mixture was stirred for about 1 h at about 40° C. to about 50° C. and then sodium bicarbonate solution was added to it. The two layers were separated and the organic layer was washed with water and sodium chloride solution. The organic layer was concentrated under vacuum followed by stripping with toluene. The residue obtained was stirred with methanol, filtered and dried. Yield: 7 g; HPLC purity: 99.4%

Example 40: Preparation of D-glucitol, 1,5-anhydro-1-C-[4-chloro-3-[(4-ethoxyphenyl)methyl]phenyl]-, (1S), Compounded with (2S)-propane-1,2-diol (1:1) monohydrate To D-glucitol, 1,5-anhydro-1-C-[4-chloro-3-[(4-ethoxyphenyl)methyl]phenyl]-(7 g) in ethyl acetate was added (S)-1,2-propanediol and water and the reaction mixture was stirred. Cyclohexane was added to the reaction mixture. The solid obtained was filtered and dried to give title compound (6.3 g). HPLC purity: 99.7%.

Example 41: Preparation of Amorphous Dapagliflozin

To a stirred solution of 2,3-butanediol solvate of dapagliflozin (2 g) in ethyl acetate, water was added and stirred for 30 min. The two layers were separated and the organic layer was concentrated under reduced pressure. Isopropyl alcohol was added to the obtained residue and the reaction mixture was concentrated under reduced pressure and degassed for 12 h. Cyclohexane was added to the obtained residue and stirred. The solid obtained was filtered to give amorphous dapagliflozin.

Example 42: Preparation of Amorphous Dapagliflozin

To a stirred solution of D-glucitol, 1,5-anhydro-1-C-[4-chloro-3-[(4-ethoxyphenyl)methyl]phenyl]-, 2,3,4,6-tetraacetate, (1S)-, (10 g) in tetrahydrofuran:methanol:water mixture, was added sodium hydroxide and the reaction mixture was stirred. The solvents were distilled out under vacuum and the residue obtained was treated with methylene dichloride, water and neutralized by using dilute hydrochloric acid. The two layers were separated and the organic layer washed with brine solution. The organic layer was concentrated and isopropyl alcohol was added to it. The organic layer was concentrated and degassed. The solid obtained was stirred with cyclohexane, filtered and dried to give amorphous dapagliflozin (7 g).

After jet-milling:

| $D_{10}$ | $D_{50}$ | $D_{90}$ |
|---|---|---|
| 2.608 µm | 15.013 µm | 64.645 µm |

Example 43: Preparation of Amorphous Dapagliflozin

To a stirred solution of D-glucitol, 1,5-anhydro-1-C-[4-chloro-3-[(4-ethoxyphenyl)methyl]phenyl]-, 2,3,4,6-tetraacetate, (1S)-, (10 g) in tetrahydrofuran:methanol:water mixture, was added sodium hydroxide and the reaction mixture was stirred for 24 h. The solvents were distilled out under vacuum and the residue obtained was treated with methylene dichloride, water and neutralized by using dilute hydrochloric acid. The two layers were separated and the organic layer washed with brine solution. The organic layer was concentrated and isopropyl alcohol was added to it. Polyethylene glycol (PEG) was added to the reaction mixture which was stirred for about 3 h. The reaction mixture was concentrated, degassed. The solid obtained stirred with cyclohexane, filtered and dried to give amorphous dapagliflozin containing less than 1% of PEG (7.5 g).

Example 44: Preparation of D-Glucitol, 1,5-anhydro-1-C-[4-chloro-3-[(4-ethoxyphenyl)methyl]phenyl]-, 2,3,4,6-tetraacetate, (1S)- from D-glucono-1,5-lactone To a mixture of D-glucono-1,5-lactone (10 g) in methylene dichloride (80 mL), hexamethyldisilazane (36.1 g) was added and the reaction mixture was refluxed. After completion of reaction, the reaction mixture was concentrated and degassed. The residue obtained was dissolved in tetrahydrofuran. 5-Bromo-2-chloro-4'-ethoxydiphenylmethane (8.7 g) was added to the reaction mixture which was cooled to about −75° C. to about −85° C. under nitrogen atmosphere. n-Butyl lithium in hexane (50 mL) was slowly added to the reaction mixture maintaining the temperature between −75° C. to about −85° C. The reaction mixture was stirred at about the same temperature and then mixture of methanol and methanesulphonic acid was added to it. The reaction mixture was quenched into sodium bicarbonate solution and extracted with ethyl acetate. The organic layer was separated, washed with saturated sodium chloride solution and concentrated under vacuum to obtain a residue. This residue was purified by a mixture of toluene and cyclohexane. To the product obtained, methylene dichloride and acetonitrile were added and the reaction mixture was cooled to about −20° C. to about −30° C. Triethylsilane (8.74 g) was added to the reaction mixture followed by addition of boron trifluoride etherate (10.67 g) maintaining temperature at about −20° C. to about −30° C. The reaction mixture was quenched in sodium bicarbonate solution. The aqueous layer was separated and extracted with ethyl acetate. The organic layer was separated, concentrated and degassed under vacuum. The thick residue obtained was dissolved in methylene dichloride and cooled to about 0° C. to about 5° C. Diisopropylethylamine, dimethylaminopyridine and acetic anhydride were added to the reaction mixture which was stirred. After completion of reaction, the reaction mixture was quenched by adding water. The aqueous layer was separated and extracted with methylene dichloride. The organic layer was separated, washed with sodium bicarbonate solution and concentrated under vacuum to obtain residue which was stripped out with methanol. The residue obtained was recrystallized with methanol and charcoal. The residue obtained was recrystallized with diisopropyl ether and then with methanol to give title compound (10 g). HPLC purity: ≥99.8%

| | Compound VIII | Impurity G | Impurity H |
|---|---|---|---|
| Before purification | 86.97% | 4.21 | 1.82 |
| 1st methanol purification | 98.76 | 0.05 | 0.08 |
| Diisopropyl ether purification | 99.08 | Not detected | 0.02 |
| 2nd methanol purification | 99.85 | Not detected | 0.01 |

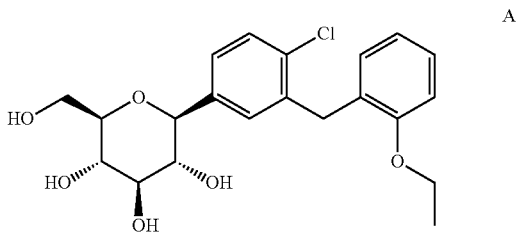 [SMILES: CCOc1ccccc1Cc1cc([C@]2(OC)O[C@H](CO)[C@@H](O)[C@H](O)[C@H]2O)ccc1Cl]

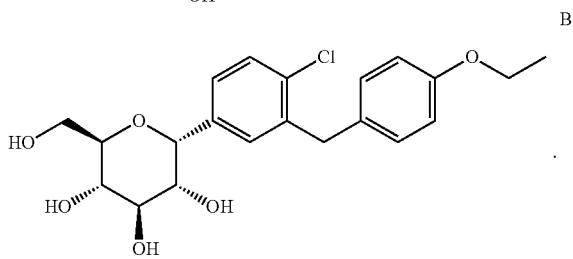

2. The process of claim 1, wherein step (c) comprises reacting the compound of formula III with the compound of formula V in the presence of a strong base to obtain a compound of formula VI; and reacting the compound of formula VI with an acid in the presence of an alcohol to obtain the compound of formula VII wherein R is an alkyl group selected from $C_{1-5}$ alkyl
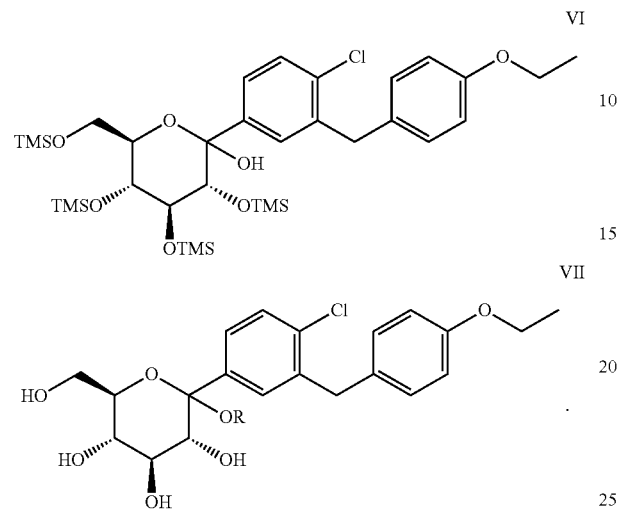

The invention claimed is:

1. A process for the preparation of dapagliflozin in amorphous form, the process comprising:
   (a) reducing a compound of formula II to a compound of formula III in the presence of a Lewis acid;

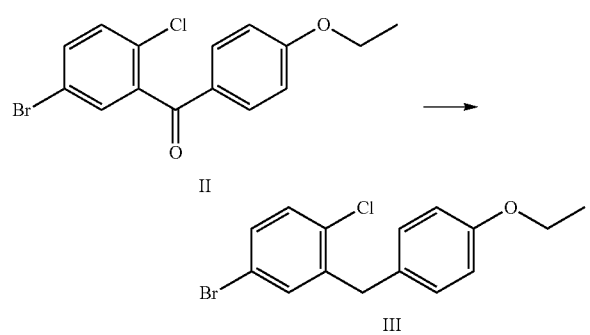

wherein the compound of formula II is prepared by reacting 5-bromo-2-chlorobenzoyl chloride with ethoxybenzene;

(b) silylating a compound of formula IV with hexamethyldisilazane to form a compound of formula V;

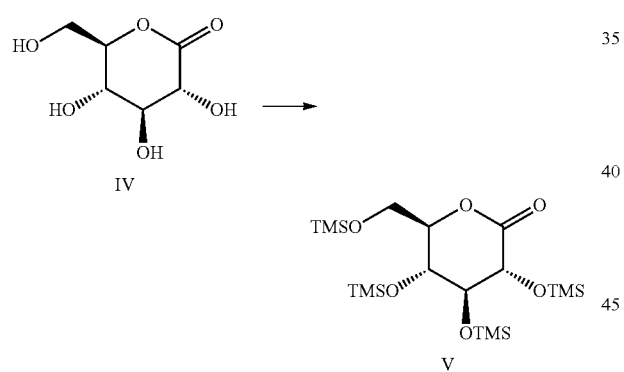

(c) reacting the compound of formula III with the compound of formula V in the presence of a strong base followed by treatment with an acid in the presence of an alcohol to prepare a compound of formula VII, wherein R is an alkyl group selected from $C_{1-5}$ alkyl;

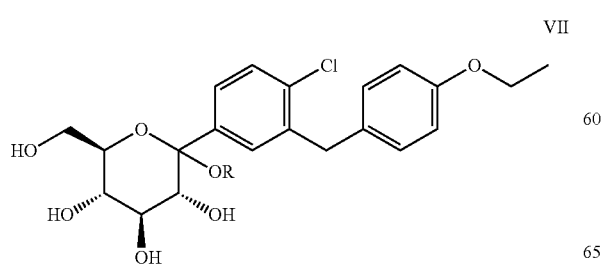

(d) converting the compound of formula VII to dapagliflozin;
   (e) acetylating dapagliflozin to give D-glucitol, 1,5-anhydro-1-C-[4-chloro-3-[(4-ethoxyphenyl)methyl]phenyl]-, 2,3,4,6-tetraacetate, (1S)-, a compound of formula VIII;

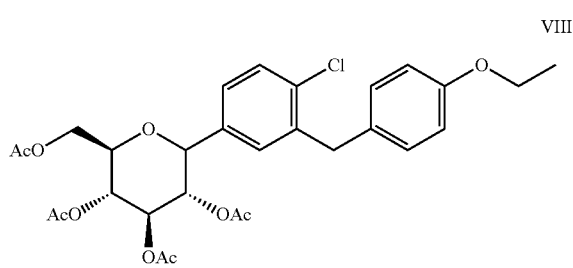 [SMILES: CCOc1ccc(Cc2cc(C3O[C@H](COC(C)=O)[C@@H](OC(C)=O)[C@H](OC(C)=O)[C@H]3OC(C)=O)ccc2Cl)cc1]

(f) purifying the compound of formula VIII by a series of crystallizing steps to obtain the compound of formula VIII with a purity of ≥99.6%, wherein the series of crystallizing steps comprises:
      (1) crystallizing the compound of formula VIII with methanol,
      (2) crystallizing the product of step (f)(1) with diisopropyl ether, and
      (3) crystallizing the product of step (f)(2) with methanol;
   (g) hydrolyzing the compound of formula VIII obtained in step (f) to give dapagliflozin;
   (h) dissolving dapagliflozin of step (g) in isopropyl alcohol to form a solution; and
   (i) recovering amorphous dapagliflozin from the solution of step (h), wherein the recovering comprises one of:
      (1) removing the isopropyl alcohol from the solution obtained in step (h) comprising concentrating the solution of step (h) and degassing; or
      (2) treating the solution of step (h) with cyclohexane,
   wherein the amorphous dapagliflozin is obtained in a purity of ≥99.8% and wherein a level of impurity A and impurity B is less than 0.15%